(12) United States Patent
Zhang

(10) Patent No.: US 11,259,762 B2
(45) Date of Patent: Mar. 1, 2022

(54) APPARATUS, SYSTEM AND METHOD FOR RADIATION BASED IMAGING

(71) Applicant: SHANGHAI UNITED IMAGING HEALTHCARE CO., LTD., Shanghai (CN)

(72) Inventor: Hongjun Zhang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 1218 days.

(21) Appl. No.: 15/318,290

(22) PCT Filed: Dec. 25, 2015

(86) PCT No.: PCT/CN2015/098891
§ 371 (c)(1),
(2) Date: Dec. 12, 2016

(87) PCT Pub. No.: WO2017/107179
PCT Pub. Date: Jun. 29, 2017

(65) Prior Publication Data
US 2018/0199898 A1    Jul. 19, 2018

(51) Int. Cl.
*A61B 6/03*   (2006.01)
*A61B 6/00*   (2006.01)
(Continued)

(52) U.S. Cl.
CPC .............. *A61B 6/4291* (2013.01); *A61B 6/00* (2013.01); *A61B 6/032* (2013.01); *A61B 6/40* (2013.01);
(Continued)

(58) Field of Classification Search
CPC ......... A61B 6/4291; A61B 6/40; A61B 6/032; A61B 6/00; A61B 6/4021; G01N 23/046; G01N 23/04; G21K 1/025
See application file for complete search history.

(56) References Cited

U.S. PATENT DOCUMENTS 4,143,273 A * 3/1979 Richey ................... A61B 6/032
378/150
4,419,585 A * 12/1983 Strauss .................. G21K 1/025
250/363.1
(Continued)

OTHER PUBLICATIONS

The extended European search report in European Application No. 15896599.6 dated Sep. 17, 2018, 8 pages.
(Continued)

*Primary Examiner* — David P Porta
*Assistant Examiner* — Shun Lee
(74) *Attorney, Agent, or Firm* — Metis IP LLC

(57) ABSTRACT

A system and method relating to a radiation based imaging are provided. The system may include a radiation source, a detector and a first grid. The detector may include a plurality of detector cells. The first grid may be located between the radiation source and the detector cells and the first grid may include a plurality of radiation transmitting sections. At least one of the plurality of detector cells may include an active area which may be configured to receive radiation from the radiation source that passes through at least one of the plurality of radiation transmitting sections of the first grid. The active area may be adjustable by adjusting the first grid. The radiation source, the first grid and the detectors cells may be operatively coupled for detecting an object. The method may include adjusting the first grid to adjust the active area of the detector.

20 Claims, 13 Drawing Sheets

(51) Int. Cl.
*G01N 23/046* (2018.01)
*G01N 23/04* (2018.01)
*G21K 1/02* (2006.01)

(52) U.S. Cl.
CPC ........... *A61B 6/4021* (2013.01); *G01N 23/04* (2013.01); *G01N 23/046* (2013.01); *G21K 1/025* (2013.01)

(56) References Cited

U.S. PATENT DOCUMENTS

| | | | |
|---|---|---|---|
| 4,637,040 A * | 1/1987 | Sohval | |
| 5,436,958 A * | 7/1995 | Taylor | G21K 1/04 |
| | | | 250/363.1 |
| 5,847,398 A | 12/1998 | Shahar et al. | |
| 6,272,207 B1 | 8/2001 | Tang | |
| 6,327,337 B1 | 12/2001 | Tsunemi | |
| 7,280,637 B1 * | 10/2007 | Chen | H01J 35/06 |
| | | | 378/136 |
| 7,924,973 B2 | 4/2011 | Kottler et al. | |
| 8,265,228 B2 | 9/2012 | Shaw et al. | |
| 2005/0167601 A1 | 8/2005 | Bruder et al. | |
| 2011/0058644 A1* | 3/2011 | Thran | A61B 6/4447 |
| | | | 378/11 |
| 2012/0153177 A1 | 6/2012 | Iwakiri et al. | |
| 2012/0181427 A1 | 7/2012 | Kaneko | |
| 2012/0183124 A1 | 7/2012 | Kaneko | |
| 2012/0201349 A1 | 8/2012 | Kaneko et al. | |
| 2013/0034209 A1 | 2/2013 | Ouchi | |

OTHER PUBLICATIONS

International Search Report for PCT/CN2015/098891 dated Oct. 8, 2016, 5 pages.

* cited by examiner

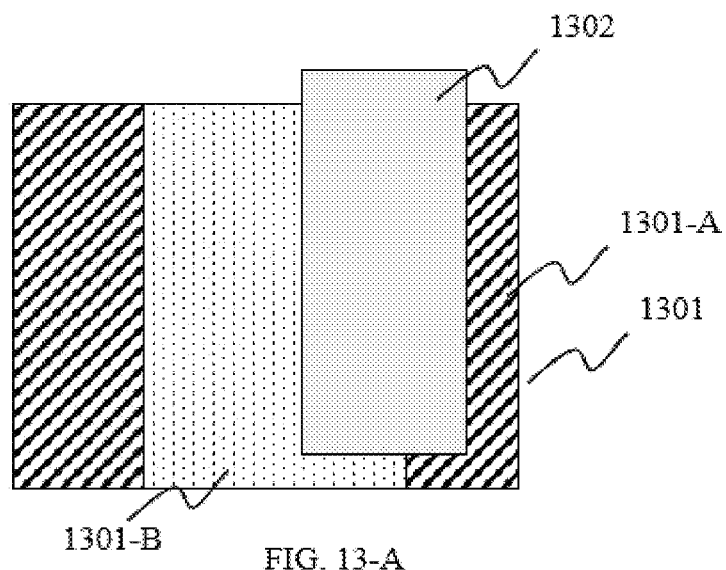
FIG. 13-A
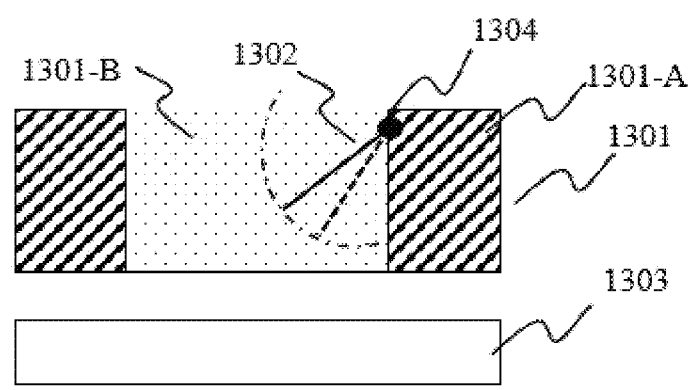
FIG. 13-B

APPARATUS, SYSTEM AND METHOD FOR RADIATION BASED IMAGING

CROSS-REFERENCE TO RELATED APPLICATIONS

This present application is a U.S. national stage under 35 U.S.C. § 371 of International Application No. PCT/CN2015/098891, filed on Dec. 25, 2015, designating the United States of America, the contents of which are hereby incorporated by reference.

FIELD OF THE INVENTION

The present disclosure generally relates to a radiation based imaging system, and more particularly, to a grid for a detector and a radiation imaging system including such a detector.

BACKGROUND

A radiation detection or imaging system may be used in many fields such as medical diagnosis and therapy, industrial production and application, scientific experiments and research, national security, etc. Generally, radiation detection or imaging may refer to a technology that may allow non-invasive observation of the interior of an object using radiation. As used herein, radiation may include a particle ray (for example, neutron, proton, electron, μ-meson, heavy ion, etc.), a photon ray (for example, X-ray, γ-ray, α-ray, β-ray, ultraviolet, laser, etc.), or the like, or any combination thereof. The information acquired by a radiation based imaging system may include, e.g., structure, density, or lesions, etc., without damaging the object. The term "object" as used herein may include a substance, a tissue, an organ, a specimen, a body, or the like, or any combination thereof. The term "target" may be used interchangeably with the term "object." For different objects to be imaged, different spatial resolutions may be needed. Thus, an apparatus, system, and method to adjust the spatial resolution are desired.

SUMMARY

In an aspect of the present disclosure, a system is provided. The system may include a radiation source, a detector, and a first grid. The radiation source may be configured to generate radiation. The detector may include a plurality of detector cells. The first grid may be located between the radiation source and the detector cells. The first grid may include a plurality of radiation transmitting sections. At least one of the plurality of detector cells may include an active area which may be configured to receive radiation from the radiation source that passes through at least one of the plurality of radiation transmitting sections of the first grid. The active area may be adjustable by adjusting the first grid. The radiation source, the first grid and the detectors cells may be operatively coupled for detecting an object. As used herein, "coupled" or "operatively coupled" may indicate that one or more components may work either alone or in combination cooperatively to achieve a function including, for example, detecting an object, adjusting a parameter of an imaging device or an image, etc.

In another aspect of the present disclosure, a method is provided. The method may include locating a first grid between a radiation source and a detector. The detector may include a plurality of detector cells and the first grid may include a plurality of radiation transmitting sections. The method may further include emitting radiation from the radiation source toward the first grid and receiving, on an active area of at least one of the plurality of detector cells, the radiation that passes through the first grid. The active area may be adjustable by adjusting the first grid. The radiation source, the first grid and the detectors cells may be operatively coupled for detecting an object.

In some embodiments, the active area may be adjustable by adjusting the position of the first grid. In some embodiments, the active area may be adjustable by tilting the first grid by an angle. In some embodiments, the angle may be any value between 0° to 360°.

In some embodiments, the system may further include a shielding device which may be configured to adjustably block the radiation source. In some embodiments, the configuration of the shielding device may be in the form of a slip sheet, a shutter, a rotation blade, or the like, or a combination thereof.

In some embodiments, the system may further include a second grid. The second grid may be located between the first grid and the detector. In some embodiments, the first grid and the second grid may be moveable relative to each other. In some embodiments, the first grid may be parallel to the second grid. In some embodiments, the first grid may be arranged at an angle to the second grid.

In some embodiments, the second grid may include a plurality of radiation transmitting portions, and at least one of the plurality of radiation transmitting portions may be coupled with an active area of a detector cell. In some embodiments, the extending direction of the radiation transmitting sections of the first grid and the extending direction of the radiation transmitting portions of the second grid may be different.

In some embodiments, the active area of a detector cell may be at least partially determined by the at least one of the plurality of radiation transmitting sections of the first grid and at least one of the plurality of radiation transmitting portions of the second grid.

In some embodiments, at least one of the plurality of radiation transmitting sections may extend in a first direction. In some embodiments, the first grid may be moveable in a second direction perpendicular to the first direction. In some embodiments, the second grid may be moveable in the first direction. In some embodiments, the first direction may be parallel, or perpendicular to, or at an oblique angle with the second direction. In some embodiments, the angle between the first direction and the second direction may be any degrees, e.g., 10°, 15°, 20°, 25°, 30°, 40°, 45°, 60°, 75°, or the like.

In some embodiments, the radiation source may include a plurality of focal spots. The trajectory of the focal spot may be continuous or discrete. In some embodiments, the continuous trajectory may be a line, a sine curve, a sawtooth wave, or other regular or other irregular shape. In some embodiments, for the discrete trajectory, the number of the positions of the focal spot may be an arbitrary value, e.g., two, three, four, five. In some embodiments, the object may be scanned by the radiation form at least two different focal spots of the radiation source.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 13-A and FIG. 13-B are schematic diagrams showing exemplary arrangements of a grid, a shielding device, and detector cells according to some embodiments of the present disclosure.

DETAILED DESCRIPTION

Figure 1:
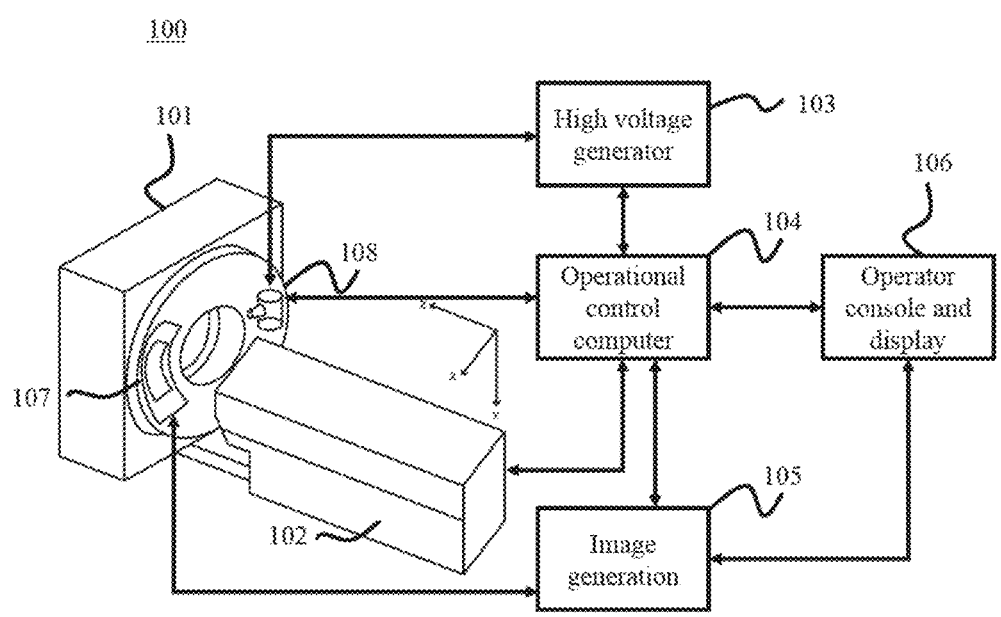
FIG. 1 illustrates a block diagram of an X-ray imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the disclosed embodiments. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

The present disclosure generally relates to a radiation based imaging system. Specifically, the disclosure provides a grid configured for adjusting an active area on a detector cell, and a radiation based imaging system including a radiation source, a detector including a plurality of detector cells, and a grid including a plurality of radiation transmitting sections. The grid may be adjusted so as to adjust an active area receiving radiation from the radiation source on the detector cells. This may allow adjustment of the spatial resolution of the imaging system such that the system may provide various spatial resolutions by adjusting, for example, the grid. The following description is provided in the exemplary contexts of an X-ray imaging system or a CT scanner for illustration purposes, and not intended for limiting the scope of the present disclosure. The system and method disclosed herein may be applicable to other radiation based imaging system. For brevity, a radiation based imaging system may be referred to as a system, or an imaging system in the present disclosure.

FIG. 1 illustrates a block diagram of the X-ray imaging system 100 according to some embodiments of the present disclosure. As shown in the figure, the X-ray imaging system 100 may include a gantry 101, an object table 102, a high voltage generator 103, an operational control computer 104, an image generator 105, and an operator console and display 106.

The gantry 101 may be configured to house the components needed to produce and detect X-rays to generate a CT image. The gantry 101 may include an X-ray tube 108 and a detector 107. It should be noted that in alternative embodiments of the present disclosure, the high voltage generator 103 may be located in the gantry 201. The X-ray tube 108 may be configured to emit radiation that may be received by the detector 107 after it passes through an object exposed in the aperture of the gantry 101. Merely by way of example, the radiation may include a particle ray, a photon ray, or the like, or any combination thereof. The particle ray may include neutron, proton, electron, μ-meson, heavy ion, or the like, or any combination thereof. The photon beam may include X-ray, γ-ray, α-ray, β-ray, ultraviolet, laser, or the like, or any combination thereof. The object may include a substance, a tissue, an organ, an object, a specimen, a body, or the like, or any combination thereof. In some embodiments, the X-ray tube 108 may be a cold cathode ion tube, a high vacuum hot cathode tube, a rotating anode tube, etc. The shape of the X-ray beam emitted by the X-ray tube 108 may be a line, a narrow pencil, a narrow fan, a fan, a cone, a wedge, an irregular shape, or the like, or any combination thereof. The shape of the detector 107 may be flat, arc-shaped, circular, or the like, or any combination thereof. The fan angle of the arc-shaped detector may be an angle from 0° to 360°. The fan angle may be fixed or adjustable according to different conditions including, for example, the desired resolution of an image, the size of an image, the sensitivity of a detector, the size or distribution of detector cells on the detector, the stability of a detector, or the like, or any combination thereof. In some embodiments, the pixels of the detector 107 may be the number of the detector cells, e.g., the number of scintillator or photodetector, etc. The pixels of the detector may be arranged in a single row, two rows, or another number of rows. The X-ray detector may be one-dimensional, two-dimensional, or three-dimensional.

The high voltage generator 103 may be configured to produce high voltage and/or current, and transmit it to the X-ray tube 108. The voltage generated by the high voltage generator 103 may range from 80 kV to 140 kV, or from 120 kV to 140 kV. The current generated by the high voltage generator may range from 20 mA to 500 mA. In alternative embodiments of the present disclosure, the voltage generated by the high voltage generator 103 may range from 0 to 75 kV, or from 75 kV to 150 kV.

The operational control computer 104 may be configured to communicate bidirectionally with the gantry 101, the tube 108, the high voltage generator 103, the object table 102, the image generator 105, and/or the operator console and display 106. Merely by way of example, the gantry 101 may be controlled by the operational control computer 104 to rotate to a desired position that may be prescribed by a user via the operator console and display 106. The operational control computer 104 may be configured to control the generation of the high voltage generator 103, for example, the magnitude of the voltage and/or the current generated by the high voltage generator 103. As another example, the operational control computer 104 may be configured to control the display of images on the operator console and display 106. For instance, the whole or part of an image may be displayed. In some embodiments, an image may be divided into several sub-portions, which may be displayed on a screen at the same time or in a certain order. According to some embodiments of the present disclosure, the user or the operator may select one or more sub-portions to display according to some conditions. Merely by way of example, the user may specify that an enlarged view of a sub-portion is to be displayed.

The operator console and display 106 may be coupled with the operational control computer 104 and the image generator 105. In some embodiments, the operator console and display 106 may be configured to display images generated by the image generator 105. In alternative embodiments, the operator console and display 106 may be configured to send a command to the image generator 105, and/or the operational control computer 104. Still in alternative embodiments of the present disclosure, the operator console and display 106 may be configured to set parameters for a scan. The parameters may include acquisition parameters and/or reconstruction parameters. Merely by way of example, the acquisition parameters may include tube potential, tube current, focal spots in the tube, recon parameters (e.g., slick thickness), scanning time, collimation/slice width, beam filtration, helical c, or the like, or any combination thereof. The reconstruction parameters may include reconstruction field of view, reconstruction matrix, convolution kernel/reconstruction filter, or the like, or any combination thereof.

The object table 102 may be configured to support a patient and move though the aperture of the gantry 101 during an examination. As shown in FIG. 1, the direction of a patient being transmitted during an examination is along the Z-direction. Depending on the ROI of the patient selected or the protocols selected, the patient may be positioned supine or prone, and either feet or head first. In some embodiments of the present disclosure, the object table 102 may be indexed between multiple scans. In some embodiments of the present disclosure, the object table 102 may be transmitted through the gantry 101 at a constant speed. The speed may relate to the length of the area to be scanned, the total scanning time, the pitch selected, or the like, or any combination thereof. In some embodiments, the object table 102 may be used to support an object other than a patient. Such a structure may move the object for examination through the X-ray imaging system. For brevity, such a structure may also be referred to a patient.

It should be noted that the description of the X-ray imaging system is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure. For example, the gantry 101 may further include a microphone, sagittal laser alignment light, patient guide lights, X-ray exposure indicator light, energy stop buttons, gantry control panels, external laser alignment lights, etc.

Figure 2:
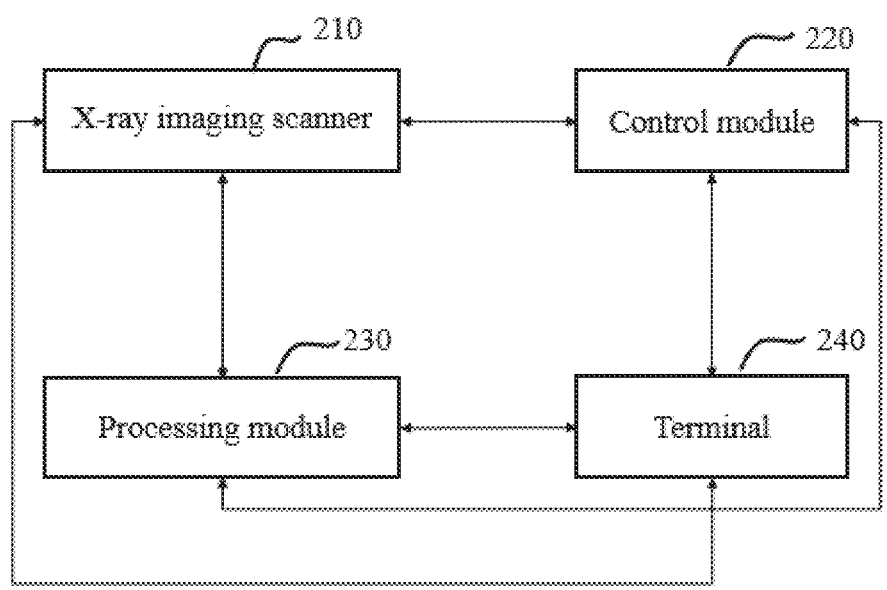
FIG. 2 is a block diagram depicting an X-ray imaging system according to some embodiments of the present disclosure.

FIG. 2 is a block diagram of an X-ray imaging system according to some embodiments of the present disclosure. It should be noted that X-ray imaging system described below is merely provided for illustrating an example of the radiation imaging system, and not intended to limit the scope of the present disclosure. The radiation used herein may include a particle ray, a photon ray, or the like, or any combination thereof. The particle ray may include neutron, proton, electron, μ-meson, heavy ion, or the like, or any combination thereof. The photon beam may include X-ray, γ-ray, α-ray, β-ray, ultraviolet, laser, or the like, or any combination thereof. For better understanding the present disclosure, an X-ray imaging system is described as an example of a radiation imaging system. The X-ray imaging system may find its applications in different fields such as medicine or industry. In some embodiments of medical diagnosis, the X-ray imaging system may be a Computed Tomography (CT) system, a Digital Radiography (DR) system or may be used in some other multi-modality system, e.g., a Computed Tomography-Positron Emission Tomography (CT-PET) system, a Computed Tomography-Magnetic Resonance Imaging (CT-MRI) system. In some embodiments of industrial application, the system may be used in internal inspection of components e.g., flaw detection, security scanning, failure analysis, metrology, assembly analysis, void analysis, wall thickness analysis, or the like, or any combination thereof.

As illustrated in FIG. 2, an X-ray imaging system may include, an X-ray imaging scanner 210, a control module 220, a processing module 230, and a terminal 240. The X-ray imaging scanner may include an X-ray generator and an X-ray detecting unit (see, for example, FIGS. 4 and 6). In some embodiments, the X-ray imaging scanner may include other components including, e.g., a gantry, a grid, a support table, etc. The control module 220 may control the X-ray imaging scanner 210, the processing module 230, and/or the terminal 240. The processing module 230 may process information received from the X-ray imaging scanner 210, the control module 220, and/or the terminal 240, and generate one or more CT images based on the information and deliver the images to the terminal 240. The terminal 240 may be configured or used to receive input and/or display output information.

The X-ray imaging scanner 210, the control module 220, the processing module 230, and the terminal 240 may be connected with each other directly, or with an intermediate module (not shown in FIG. 2). The intermediate module may be a visible component or an invisible field (radio, optical, sonic, electromagnetic induction, etc.). The connection between different modules may be wired or wireless. The wired connection may include using a metal cable, an optical cable, a hybrid cable, an interface, or the like, or any combination thereof. The wireless connection may include using a Local Area Network (LAN), a Wide Area Network (WAN), a Bluetooth, a ZigBee, a Near Field Communication (NFC), or the like, or any combination thereof.

It should be noted that the above description about the radiation system is merely an example. Obviously, to those skilled in the art, after understanding the basic principles of the connection between different modules, the modules and connection between the modules may be modified or varied without departing from the principles. The modifications and variations are still within the scope of the present disclosure described above. In some embodiments, these modules may be independent, and in some embodiments, part of the modules may be integrated into one module to work together.

The X-ray imaging scanner 210 may be configured or used to scan an object (not shown in FIG. 2) under examination and generate the source data of an X-ray image. The object may be a substance, a tissue, an organ, an object, a specimen, a body, or the like, or any combination thereof. In some embodiments, the object may include a head, a breast, a lung, a pleura, a mediastinum, an abdomen, a colon, a small intestine, a bladder, a gallbladder, a triple warmer, a pelvic cavity, a backbone, extremities, a skeleton, a blood vessel, or the like, or any combination thereof. The X-ray generating unit may be configured or used to generate X-rays to traverse the object under examination. The X-ray generating unit may include an X-ray generator, a high-voltage tank, and/or one or more other accessories. Additionally, the X-ray generator may include one or more X-ray tubes which may emit X-rays by an X-ray tube. Moreover, the X-ray generating unit may be a cold cathode ion tube, a high vacuum hot cathode tube, a rotating anode tube, etc. The shape of the X-ray beam emitted may be a line, a narrow pencil, a narrow fan, a fan, a cone, a wedge, or the like, or an irregular shape, or any combination thereof. The X-ray tube in the X-ray generating unit may be fixed at a point and it may translate or rotate in some scenarios. In some embodiments, the focal spot of the X-ray beam may be in a fixed position inside the X-ray generator. In some embodiments, the focal spot of the X-ray beam may be movable inside the X-ray generator, and the trajectory of the focal spot may be continuous or discrete. In some embodiments, the continuous trajectory may be a line, a sine curve, a sawtooth wave, or other regular or other irregular shape. In some embodiments, for the discrete trajectory, the number of the positions of the focal spot may be an arbitrary value, e.g., two, three, four, five. The positions may be in a line, in a plane or in a 3D space. In some embodiments, the interval between each two positions may be equivalent or not.

The X-ray detecting unit may be configured to receive the X-rays emitted from the X-ray generating unit or other radiation source. The X-ray beams from the X-ray generating unit may traverse the object under examination. After receiving the X-rays, the X-ray detecting unit may generate the source data of an X-ray image of the object under examination. The term "source data" may refer to the data that may be detected by the X-ray detecting unit, and/or that may be transformed to the image data according to an imaging processing procedure based on, for example, an algorithm. As used herein, the term "image data" may refer to the data that may be used to construct an image. The X-ray detecting unit may be configured to receive X-rays and generate the source data of an X-ray image of the object under examination. The X-ray detecting unit may include an X-ray detector, and/or one or more other components. The shape of the X-ray detector may be flat, arc-shaped, circular, or the like, or any combination thereof. The fan angle of an arc-shaped detector may be an angle from 0° to 360°. The fan angle may be fixed or adjustable according to different conditions including, for example, the desired resolution of an image, the size of an image, the sensitivity of a detector, the stability of a detector, or the like, or any combination thereof. In some embodiments, the X-ray detector may be one-dimensional, two-dimensional, or three-dimensional.

In some embodiments, there may be a collimator located or placed between the X-ray generating unit and an object (or referred to as a target). In some embodiments, there may be one or more grids between the target and the detecting unit. The grids may be configured to absorb and/or block the scattered radiation from the object under examination. The number of the grids may be one, two, three, or any other value. In some embodiments, the grids may physically contact or be in direct contact with each other. In some embodiments, the grids may be spaced apart from each other. In some embodiments, a grid and a detector may physically contact or be in direct contact with each other or be spaced apart from each other. In some embodiments, the grids may be parallel to a detector. In some embodiments, the grids may be placed at an angle to the detector. The angle may be adjustable from 0° to 360°. In some embodiments, the grids may be parallel to one or more other grids. In some embodiments, the grids may be placed with an adjustable angle from 0° to 360° with each other.

It should be noted that the above description about the X-ray image unit is merely an example according to the present disclosure. Obviously, to those skilled in the art, after understanding the basic principles of the X-ray image unit, the form and details of the X-ray image unit may be modified or varied without departing from the principles. The modifications and variations are still within the scope of the present disclosure described above.

The control module 220 may be configured to control the X-ray imaging scanner 210, the processing module 230, the terminal 240, or one or more other units or devices in the system according to some embodiments of the present disclosure. The control module 220 may communicate with (by way of, for example, receiving information from and/or sending information to) the X-ray imaging scanner 210, the processing module 230, and/or the terminal 240. In some embodiments, the control module 220 may provide a certain voltage, and/or certain current to the X-ray imaging scanner 210 for scanning. The voltage and/or current may be different for different targets including, for example, people of different age, weight, height, etc.

In some embodiments, the control module 220 may control the position of the focal spot of an X-ray beam, the motion speed of the focal spot, the position of one or more grids, or the like, or any combination thereof. See, for example, FIG. 4 and the description thereof. In some embodiments, the control module 220 may receive a command from the terminal 240 provided by, e.g., a user. Exemplary commands may include a scanning time, a location of the object to be examined, a rotating speed of the gantry, or the like, or any combination thereof. The control module 220 may control the processing module 230 to select different algorithms to process the source data of an X-ray image.

The control module 220 may transmit a command to the terminal 240. Exemplary commands may include the size of an image, the location of an image, or the duration of an X-ray image to be displayed on a display screen. In some embodiments of the present disclosure, the X-ray image may be divided into several sub-portions for display, and the control module 220 may control the number of the sub-portions.

It should be noted that the above description about the control unit is merely an example according to the present disclosure. Obviously, to those skilled in the art, after understanding the basic principles of the control unit, the form and details of the control module 220 may be modified or varied without departing from the principles. The modifications and variations are still within the scope of the present disclosure described above.

The terminal 240 may be configured or used to receive input and/or display output information. The input and/or output information may include programs, software, algorithms, data, text, number, images, voice, or the like, or any combination thereof. For example, a user or an operator may input an initial parameter or condition to initiate a scan. Exemplary parameters or conditions may include the scanning time, the location of the object for scanning, the rotating speed of the gantry, or the like, or a combination thereof. As another example, some information may be imported from an external source, such as a floppy disk, a hard disk, a USB flash drive, a wireless terminal, or the like, or any combination thereof. The terminal 240 may show the X-ray image of an object from the processing module 230 to the user. The terminal 240 may receive information from the control module 220 to adjust some parameters for displaying. Exemplary parameters may include the size of an image, the location of an image, the time duration of an image remains on a display screen, or the like, or a combination thereof. The terminal 240 may display the whole or part of an X-ray image. In some embodiments, an X-ray image may be divided into several portions, which may be display on a screen at the same time or in a certain order. In some embodiments of the present disclosure, the user or the operator may select one or more portions for display.

It should be noted that the above description about the display unit is merely an example according to the present disclosure. Obviously, to those skilled in the art, after understanding the basic principles of the display unit, the form and details of the display unit may be modified or varied without departing from the principles. The modifications and variations are still within the scope of the present disclosure described above.

It should be noted that the above description of the X-ray imaging system is merely provided for the purposes of illustration, and not intended to limit the scope of the present disclosure. For persons having ordinary skills in the art, multiple variations and modifications may be made under the teachings of the present disclosure. For example, the assembly and/or function of the X-ray imaging system may be varied or changed according to specific implementation scenarios. Merely by way of example, some other components may be added into the X-ray imaging system, such as a patient positioning unit, a high-voltage tank, an amplifier unit, a storage unit, an analog-to-digital converter, a digital-to-analog converter, an interface circuit, or the like, or any combination thereof. Note that the X-ray imaging system may be a traditional or a single-modality system, or a multi-modality system including, e.g., a Positron Emission Tomography-Computed Tomography (PET-CT) system, a Computed Tomography-Magnetic Resonance Imaging (CT-MRI) system, a remote medical X-ray imaging system, etc. However, those variations and modifications do not depart from the scope of the present disclosure.

Figure 3:
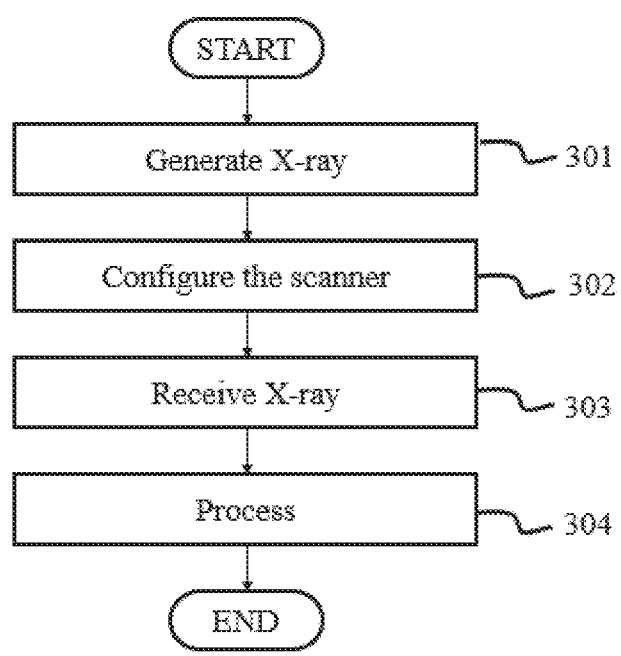
FIG. 3 is a flowchart illustrating a process for X-ray imaging according to some embodiments of the present disclosure.

FIG. 3 depicts a flowchart illustrating the process of an X-ray scanning according to some embodiments of the present disclosure. It should be noted that X-ray scanning process described below is merely provided for illustrating an example of the radiation imaging, and not intended to limit the scope of the present disclosure.

As illustrated in FIG. 3, in step 301, X-ray beams may be generated. X-ray beams may be generated by the X-ray generating unit, or another radiation source. In some embodiments, an X-ray tube in the X-ray generating unit may emit X-ray beams forming the shape of a line, a narrow pencil, a narrow fan, a fan, a cone, a wedge, or the like, or an irregular shape, or any combination thereof. The fan angle of the X-ray beams may be a certain value within the range from 0° to 360°. In some embodiments, before step 301, there may be some parameters to be set by a user or an operator. Exemplary parameters may include the parameters for the gantry, for the X-ray tube, for the X-ray detector, for a display device, or for one or more other devices or units in or communicated with the system. Merely by way of example, a user may set parameters including a certain voltage, and/or a certain current for people of a certain age, weight, height, etc. In some embodiments, the gantry may be adjusted to a certain rotating speed according to some parameters. In some embodiments, the beam shape and the angle of a fan beam may be selected based on one or more parameters. The type of the X-ray detector may be selectable based on one or more parameters. It should be noted that the above description about the parameters is merely provided for the purposes of illustration, and not intended to limit the scope of the present disclosure. For persons having ordinary skills in the art, multiple variations and modifications about the parameters that are set may be made under the teachings of the present disclosure.

In step 302, the X-ray imaging scanner may be configured. In some embodiments, before scanning an object, noise in the system may be measured. In some embodiments, there may be one or more parameters to be adjusted according to a condition including, for example, a spatial resolution, sensitivity, stability, or the like, or any combination thereof. Exemplary parameters may include the position of the focal spot of the X-ray beam, the motion speed of the focal spot, the position of the grids, or the like, or any combination thereof. In some embodiments, the spatial resolution may be adjusted or improved for a certain object (for example, a certain organ) than others. This may be achieved by, for example, decreasing the area for receiving radiation in a pixel of an X-ray detector (e.g., a detector cell), referred to as an active area of a pixel (for example, a detector cell). In some embodiments, the active area may be adjusted by way of adjusting, for example, the position of the focal spot of the X-ray beam, the position(s) of the grid(s), the distance of a grid from the X-ray source, the angle formed by a grid and an X-ray detector, the angle formed by two grids, the position of a grid relative to another grid, or the like, or any combination thereof. It should be noted that the step 301 and step 302 described herein is merely an example, and not intended to limit the scope of the present disclosure. For persons having ordinary skills in the art, multiple variations and modifications in the form and structure may be made under the teaching of the present disclosure. For example, the order of the steps may be reversed, i.e., the X-ray imaging scanner may be configured first, and the focal spot of the X-ray beam and the grids may be adjusted to the proper positions and then, the X-rays may be generated.

In step 303, the X-ray beams may be received by, for example, the X-ray detecting unit of the X-ray imaging scanner 210. In some embodiments, the X-ray detector of the X-ray detecting unit may receive X-ray beams impinging thereon. The impinging X-ray beams may include the X-ray beams that have traversed an object under examination, the X-ray beams directly emitted from the X-ray generating unit, and/or the X-ray beams from one or more other radiation sources. Parts of the X-ray beams emitted from the X-ray generating unit may be blocked and/or absorbed by one or more grids located before the X-ray detector. In some embodiments, the X-ray beams may first be converted to light energy by, for example, a scintillator, and then an electrical signal may be produced therefrom by, for example, a photodiode. The electrical signal may be transmitted to, for example, the processing module 230.

It should be noted that the above description about the signal conversion is merely provided for the purposes of illustration, and not intended to limit the scope of the present disclosure. For persons having ordinary skills in the art, multiple variations and modifications in the form and structure may be made under the teaching of the present disclosure. For example, the scintillators may be replaced by other components that may absorb the radiation and generate light energy, and the photodiodes may be replaced by other components which may be capable of converting the light energy to electrical signals.

The received signals may be processed in step 304. In some embodiments, the processing module 230 may process the data from the X-ray detector to generate the X-ray image data of an object under examination. The process may involve an algorithm including, for example, a filtered back projection, an n-PI, a tomosynthesis, or the like, or a combination thereof. In this step, the image may be calibrated using a calibration algorithm. In some embodiments, the image data, the calibrated data, and/or the received signals from the processing module 230 may be stored in a storage unit and/or device. A storage unit or device may store information by the way of electric, magnetic, or optical energy, etc. The device that store information by the way of electric energy may include Random Access Memory (RAM), Read Only Memory (ROM), or the like, or any combination thereof. The device that stores information by the way of magnetic energy may include a hard disk, a floppy disk, a magnetic tape, a magnetic core memory, a bubble memory, a USB flash drive, or the like, or any combination thereof. The device that store information by the way of optical energy may include CD (Compact Disk), VCD (Video Compact Disk), or the like, or any combination thereof. The method to store information may include sequential storage, link storage, hash storage, index storage, or the like, or any combination thereof.

The image data or the calibrated image may be shown to the user or operator via the terminal 240. In some embodiments, the X-ray image of the object may be printed. In some embodiments, the calibrated or uncalibrated image data of the object may be transmitted to a third party including, for example, a doctor. The doctor may make an assessment or decision based on the data received.

It should be noted that the above description about the process of X-ray scanning is merely an example according to the present disclosure. Obviously, to those skilled in the art, after understanding the basic principles of the process of X-ray scanning, the form and details of the process may be modified or varied without departing from the principles. In some embodiments, other steps may added in the process. For example, the results of the processing may be displayed on some devices, and the intermediated data and/or the final data of the process may be stored in the process. The modifications and variations are still within the scope of the present disclosure described above.

Figure 4:
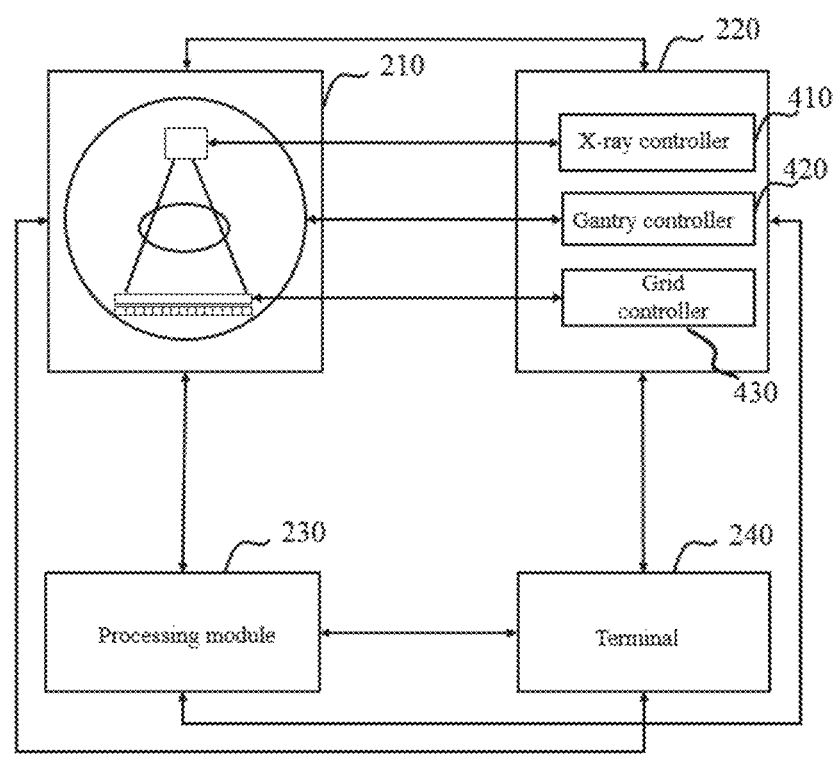
FIG. 4 is an exemplary schematic diagram of an X-ray imaging scanning system according to some embodiments of the present disclosure.

FIG. 4 is an exemplary schematic diagram of the CT scanning system according to some embodiments of the present disclosure. As described elsewhere in the disclosure, the control module 220 may be configured to control the X-ray imaging scanner 210 in order to generate data for further processing by the processing module 230. During the operation of the scanning, different parts of the X-ray imaging scanner 210 may be controlled separately by respective controllers. As shown in FIG. 4, the control module 220 may include an X-ray controller 410, a gantry controller 420, and a grid controller 430.

The X-ray controller 410 may provide power and timing signals to an X-ray source 108. In some embodiments, the X-ray source 108 may include more than one focal point, in which case the radiation received by the detector 107 may come from different focal spots that a number of beam paths are produced during scanning. Thus, the one or more focal spots generating the X-ray may be controlled by the X-ray controller 410 under certain conditions in the scanning. During a scanning to acquire X-ray projection data, the gantry and the components mounted thereon may rotate about a center of rotation. The rotational speed and position of the gantry 101 may be controlled by the gantry controller 420. In the gantry, the X-ray source 108 may project an X-ray beam toward a detector 107 or a collimator on the opposite side of the gantry.

In some embodiments, the detector 107 may be formed by a plurality of detector cells and a data acquisition system (not shown in FIG. 4). The plurality of detector cells may sense the projected X-rays that pass through a subject, and the data acquisition system may convert the data to digital or analog signals for subsequent processing. A detector cell may produce a signal that may represent the intensity of an impinging X-ray beam. If an X-ray beam passes through the subject before reaching the detector cell, the intensity of the impinging X-ray beam may be attenuated. In some embodiments, the working condition of a detector cell may be controlled by the gantry controller 420. In some embodiments, the gantry controller 420 may control or adjust the sensitivity of a detector cell. For example, the gantry controller 420 may be configured to adjust the detector cell(s) to provide a higher sensitivity when scanning a structure/tissue of a small dimension. In another example, the sensitivity may be adjusted when the X-ray beam is blocked or partially blocked by, for example, a grid. As used herein, the sensitivity of a detector cell may represent the ability to detect a radiation signal with certain intensity. The sensitivity of a detector cell may be related to, for example, the voltage applied on the detector cell, the temperature of the detector cell, the material of the detector cell, or the like, or a combination thereof.

One or more grids may be arranged or located between the X-ray source 108 and the detector 107 in order to change the detection of radiation in some manner. In some embodiments, the grids may be controlled along with the detector 107. In some embodiments, one or more grids may be controlled in relation with the focal points of the X-ray source 108. For instance, different focal spots may be applied along with different grid arrangements. The grid arrangement may be controlled by the grid controller 430. Exemplary grid arrangements may include changing the number of grids, selecting or replacing the types of grids, adjusting the movement of one or more grids, or the like, or a combination thereof. Changing the number of grids may include increasing or decreasing grids used in the scanning. Considering that different configurations of the grids may result in different scanning effect, the type of the grids may be selected or replaced in some situations. As used herein, the type of a grid may correspond or relate to the dimension of a radiation transmitting section, the shape of a radiation transmitting section, the thickness of the grid, the material(s) of the grid, or the like, or a combination thereof. A grid may include a plurality of radiation transmitting sections, or referred to as radiation transmitting portions. The dimension of radiation transmitting sections (or radiation transmitting sections) of a grid may affect the spatial resolution. As used herein, the radiation transmitting section or radiation transmitting portion may refer to the area on a grid that radiation may not be absorbed or blocked. For instance, the radiation transmitting section or radiation transmitting portion may be an opening or slit on the grid through which a radiation beam may pass through without being absorbed or blocked. The radiation transmitting section or portion may have a shape of a circle, a square, a rectangle, or any shape that is regular or irregular.

The dimension of the radiation transmitting sections may represent the width, length, radius, or area, of the radiation transmitting sections. The radiation transmitting section (or portion) may have a characteristic dimension. As used herein, the characteristic dimension of the radiation transmitting section (or portion) may be the smallest dimension of the radiation transmitting section (or portion) among its dimensions including, for example, the length, the width, the radius, etc. Merely by way of example, for a circular radiation transmitting section (or portion), the characteristic dimension is the radius of the radiation transmitting section (or portion). As another example, a square radiation transmitting section (or portion), the characteristic dimension is the length of an edge of the radiation transmitting section (or portion). As a further example, a rectangular radiation transmitting section (or portion), the characteristic dimension is the length of the shorter edge of the radiation transmitting section (or portion). As still a further example, for a radiation transmitting section (or portion) of an irregular shape, the characteristic dimension is the smallest dimension among the one or more dimensions describing or defining the shape of the radiation transmitting section (or portion). The characteristic dimension of a radiation transmitting section may be several orders higher than the wavelength of the radiation. For instance, the characteristic dimension of a transmitting section may be at least $10^{\wedge}5$ times, or at least $10^{\wedge}6$ times, or at least $10^{\wedge}7$ times, or at least $10^{\wedge}8$ times, or at least $10^{\wedge}9$ times, or at least $10^{\wedge}10$ times, or at least $10^{\wedge}11$ times of the wavelength of the radiation used in an imaging system. The characteristic dimension of a radiation transmitting section may be comparable to the dimension of a detector cell. For instance, assuming the dimension of a detector is 1 mm, the characteristic dimension of a radiation transmitting section may be 0.1 mm, or 0.2 mm, or 0.3 mm, or 0.4 mm, or 0.5 mm, or 0.6 mm, or 0.8 mm.

The grid may include one or more radiation absorbing sections, or referred to as radiation absorbing portions. As used herein, the radiation absorbing section or radiation absorbing portion may refer to the area on a grid that radiation may be absorbed or blocked. For instance, radiation impinging on a radiation absorbing section or radiation absorbing portion may not pass through the grid.

In some embodiments, the radiation transmitting sections may be adjusted using a shielding device. The shielding device may be coupled to the grid. The shielding device may be a radiation blocker or absorber set in/on the grid, or coupled without contacting the grid. The shielding device may be made of lead, gold, tungsten, depleted uranium, thorium, barium sulfate, tantalum, iridium, osmium, or the like, or any combination thereof. The configuration of the shielding device may be in the form of a slip sheet, a shutter, a rotation blade, or the like, or a combination thereof. Merely by way of example, a grid may include a plurality of radiation transmitting sections; a shielding device may include multiple rotation blades; each of at least some of the radiation transmitting sections may be associated with a rotation blade of the shielding device; the radiation transmitting sections of the grid with associated rotation blades may be adjusted by rotating the rotation blades such that the areas of these radiation transmitting sections allowing the passage of radiation may be adjusted.

In some embodiments, the shielding device is not attached to or does not otherwise contact the grid. In some embodiments, a shielding device may be movably attached to a grid. As used herein, a movable attachment may indicate that the shielding device, or a portion thereof, may move relative to the grid to which the shielding device attaches. For instance, a shielding device may include a plurality of shutters; the shutters may be movably attached to the grid.

The shielding device, or a portion thereof, may at least partially cover a radiation transmitting section or portion. The coverage may be adjusted so that the open area of the radiation transmitting section or portion that may allow passage of radiation may be adjusted. The coverage may range from no coverage to full coverage. As indicated herein, no coverage may indicate that the entire radiation transmitting section or portion is available to allow passage of radiation. As indicated herein, full coverage may indicate that the entire radiation transmitting section or portion is covered by a shielding device or a portion thereof (for example, a shutter of the shielding device), and therefore no portion of the radiation transmitting section or portion is available to allow passage of radiation.

The movement of a grid may lead to the movement of the radiation transmitting sections on the grid. Merely by way of example, the movement of a grid may include a motion along a certain direction (e.g., the Z-direction, or any direction on the x-y plane), a tilting with respect to a certain axis, or the like, or a combination thereof. The motion of the grid along a certain direction may cause the motion of the radiation transmitting sections on the grid, and the active area of a detector cell may also change. The tilting of a grid may also lead to a change of the active area of a detector cell. As used herein, the active area of a detector cell may refer to the area that receives radiation transmitted through the object and/or the grid(s) detectable by the detector cell. In some embodiments, an active area of a detector cell may relate to the spatial resolution of the imaging system. For instance, a small active area of a detector cell may correspond to higher spatial resolution of the scanning system. In some embodiments, an active area of a detector may relate to the resolution of a reconstructed image. For instance, the smaller active area of a detector may correspond to higher resolution of a reconstructed image.

The X-ray controller 410, the gantry controller 420, and the grid controller 430 may be configured to operate systematically. Put another way, the operation of an X-ray source (e.g., the focal points), the operation of the gantry (e.g., the rotation), and the arrangement of the one or more grids (e.g., the motion, the rotation) may be operatively coupled with each other to provide, for example, a desired spatial resolution for subsequent processing. For example, the operation of an X-ray source, the operation of the gantry, and the arrangement of the one or more grids may be conducted in a coordinated way to achieve an adjustable spatial resolution. In some embodiments, one of the operation of an X-ray source, the operation of the gantry, and the arrangement of the one or more grids may be selectively conducted to change the spatial resolution.

Merely by way of example, a radiation-based imaging system may include two grids, a first grid and a second grid, a radiation source (for example, an X-ray source), and a detector. The detector may include a plurality of detector cells. The two grids may be located between the radiation source and the detector. The spatial resolution of the system may be adjusted by adjusting the active areas of detector cells of the detector. The adjustment may be achieved by adjusting a radiation transmitting portion of one grid and/or a radiation transmitting section of the other grid to change the area that may allow radiation to pass through. For a radiation beam to pass through both grids, the radiation beam may need to pass through an area (referred to as an overlapping area) where a radiation transmitting portion of one grid and/or a radiation transmitting section of the other grid overlap along the path of the radiation beam. For instance, the adjustment may be achieved by adjusting the overlapping area by moving one or both grids, or tilting one or both grids. Two or more way for adjustment may be combined.

As another example, the imaging system may include a grid. The spatial resolution of the system, or the active areas of detector cells of the detector, may be adjusted by adjusting the area of a radiation transmitting portion or section that may allow radiation to pass through. For instance, the adjustment may be achieved by tilting a grid by an angle, or moving the position of the grid.

As a further example, the imaging system may include a shielding device. The shielding device may be configured to block at least part of the radiation from the radiation source. The spatial resolution of the imaging system may be adjusted by adjusting the shielding device. The amount of the radiation blocked may be adjusted by adjusting the shielding device. In some embodiments, the shielding device may be a radiation blocker or absorber set in/on the grid, or coupled without contacting the grid. The shielding device may be made of lead, gold, tungsten, depleted uranium, thorium, barium sulfate, tantalum, iridium, osmium, or the like, or any combination thereof. The configuration of the shielding device may be in the form of a slip sheet, a shutter, a rotation blade, or the like, or a combination thereof. See relevant description regarding the shielding device elsewhere in the present disclosure.

One or more of the ways for adjusting the spatial resolution of the imaging system may be used alone, or in combination. For example, the adjustment of the position of the grid and the adjustment of the shielding device on the grid may be used cooperatively to achieve a desired spatial resolution.

It should be noted that the description of the CT scanning system is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure. For example, the effect of the X-ray controller 410, the gantry controller 420, and/or the grid controller may be achieved by a single integrated controller. Additionally, the controllers may communicate with each other through a wired connection, or the communication may also be realized in a wireless way.

Figure 5:
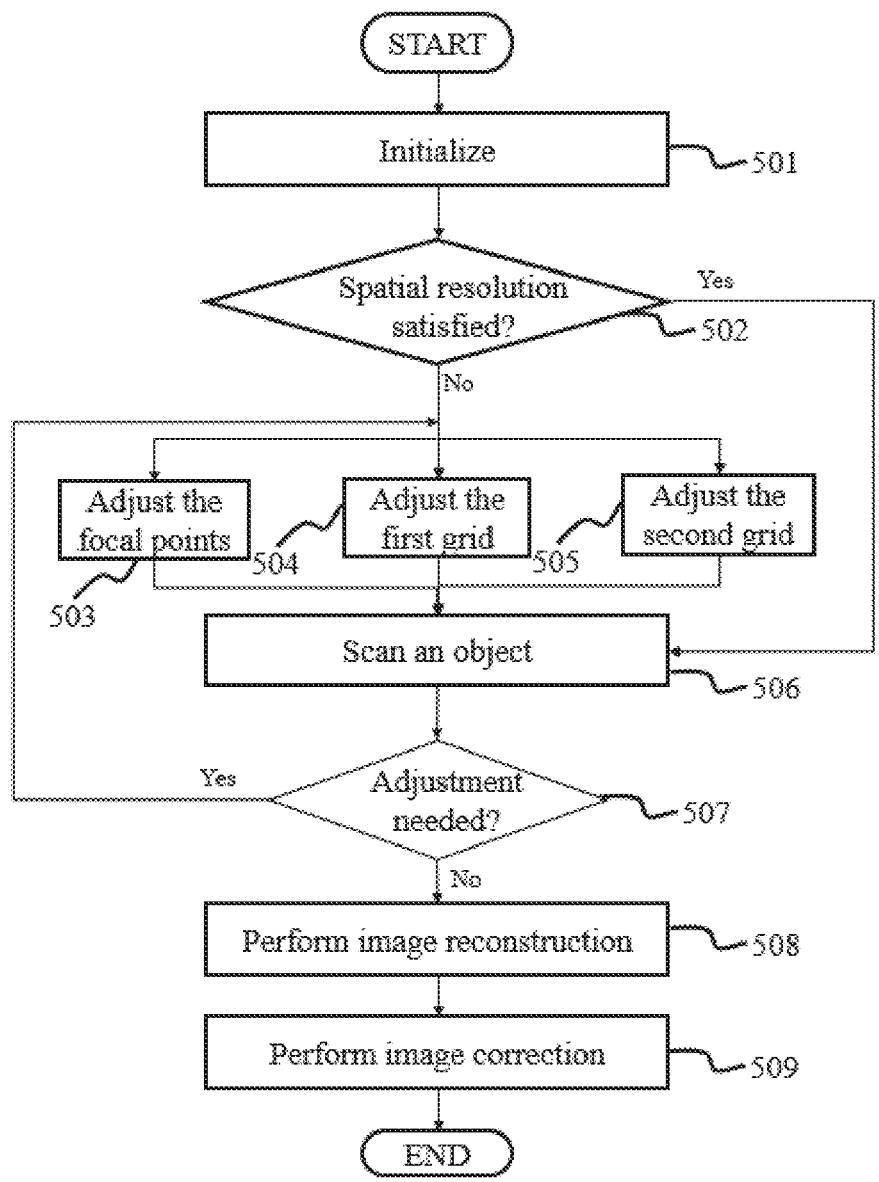
FIG. 5 is a flowchart of an exemplary process for X-ray scanning according to some embodiments of the present disclosure.

FIG. 5 is an exemplary flowchart of an exemplary process for CT scanning according to some embodiments of the present disclosure. At step 501, the CT scanner may be initialized. During the initialization, a plurality of parameters may be set. Exemplary parameters to be initialized may include, for example, the parameters relating to the X-ray source, the parameters relating to the detector, the parameters relating to the detector cells, the parameters relating to the gantry and components mounted thereon, the parameters relating to the grids, the parameters relating to the reconstruction process, or the like, or a combination thereof. The parameters relating to the X-ray source may include the shape of the X-ray beams including, for example, a line, a narrow pencil, a narrow fan, a cone, a wedge, an irregular shape, or the like, or a combination thereof, emitted by the X-ray tube. In some embodiments, a plurality of focal spots may be configured to emit the X-rays in the X-ray source. The size and/or position of the focal spots may be initialized to for subsequent processing. The CT scanner may also include a shielding device configured to adjustably block the radiation from the X-ray source. The parameters relating to the detector may include the shape of the detector including, e.g., flat, arc-shaped, circular, etc. The parameters relating to the detector cells may include the size and/or the sensitivity of the cell. The parameters relating to the gantry and components mounted thereon may include the rotational speed of the gantry. The parameters relating to the grids may include the arrangement of the grids, such as, the number of the grids. The parameters relating to the reconstruction process may include the shape and/or size of voxels, the algorithm for calculating the values of respective voxels, the algorithm for reconstructing an image data (e.g., iterative projection, filtered back projection, etc.), or the like, or a combination thereof.

A spatial resolution of the scanning system may be assessed at step 502. If a desired spatial resolution is satisfied, an object may be scanned in step 506. If the desired spatial resolution is not satisfied, one or more parameters may be adjusted, Merely by way of example, in order to achieve higher spatial resolution in the scanning system, at steps 503, 504, and 505, the size and/or position of the focal spots may be adjusted, the shielding device, and/or the first grid and/or the second grid (if applicable) may be adjusted. The adjustment may be such that the amount and/or distribution of radiation impinging on detector cells of the detector are changed to provide the desired spatial resolution. The active area of a detector cell may receive radiation from a radiation source that passes through at least one of a plurality of radiation transmitting sections or portions of a grid. See relevant description elsewhere in the present disclosure. Various adjustments may be such that active areas of detector cells are changed to provide the desired spatial resolution. For instance, if a grid is used, the adjustment may be achieved by adjusting the area of a radiation transmitting portion or section that may allow radiation to pass through. For instance, the adjustment may be achieved by tilting a grid by an angle, or moving the position of the grid. If a plurality of grids are used, the adjustment may be achieved by adjusting a radiation transmitting portion of one grid and/or a radiation transmitting section of the other grid to change the area that may allow radiation to pass through. For a radiation beam to pass through both grids, the radiation beam may need to pass through an area where a radiation transmitting portion of one grid and/or a radiation transmitting section of the other grid overlap along the path of the radiation beam. For instance, the adjustment may be achieved by adjusting the overlapping area by moving one or both grids, or tilting one or both grids, Two or more ways for adjustment may be combined. For instance, the adjustment of the shielding device may be combined with the adjustment of one or more grids to achieve a desired spatial resolution.

Merely by way of example, two grids are included. The adjustment of the first and/or the second grids may include arranging the positions of the first grid and/or the second grid. For example, the first grid may be arranged to move along a first direction, and/or the second grid may be arranged to move along a second direction. The first direction may be parallel, or perpendicular to, or at an oblique angle with the second direction. For instance, the angle between the first direction and the second direction may be any degrees, e.g., 10°, 15°, 20°, 25°, 30°, 40°, 45°, 60°, 75°, or the like. In another example, the first grid may be arranged to tilt about an axis by a certain angle, and/or the second grid may be arranged to move along a certain direction. In a further example, the first grid may be arranged to tilt about an axis by a first angle, and/or the second grid may be arranged to tilt about another axis by a second angle. As used herein, the first direction/angel may be either the same as or different from the second direction/angel. In some embodiments, the extending direction of the radiation transmitting sections on the first grid and the second grid may be different. For example, the extending direction of the radiation transmitting sections on the first grid may be perpendicular to the extending direction of the radiation transmitting sections on the second grid. In some embodiments, the term "radiation transmitting section" may be used in association with the first grid, and the term "radiation transmitting portion" may be used in association with the second grid. In some embodiments, the first grid may be arranged to move along the direction perpendicular to the extending direction of the radiation transmitting sections on the first grid (e.g., X-direction, or Y-direction), and the second grid may be arranged to move along the direction perpendicular to the extending direction of the radiation transmitting sections on the second grid (e.g., Z-direction). In some embodiments, the adjustment of the focal point, the first grid, and the second grid may be operatively coupled with each other. For example, the position of the focal spot may be represented by function $f(x, y, z)$, the position of the first grid may be represented by function $f_1(x_1, y_1, z_1)$, and the position of the second grid may be represented by function $f_2(x_2, y_2, z_2)$. By controlling the position of the focal point, the position of the first grid, and the position of the second grid, the active area on a respective detector cell may be adjusted, which may result in a specific spatial resolution. The adjustment may be expressed as $$Q(S,P)=\text{Control}[f(x,y,z), f_1(x_1,y_1,z_1), f_2(x_2,y_2,z_2)], \quad (1)$$

where Q(S, P) is the controlling process, Control is the controlling method. The detailed descriptions about the adjustment may be found elsewhere in the present disclosure.

An object may be scanned at step 506. Another assessment may be conducted at step 507. If another adjustment is needed, parameters of interest, such as, the position of the focal points, the parameters relating to the first and/or the second grid may be adjusted. If no adjustment is needed, image reconstruction may be performed at step 508. Merely by way of examples, a plurality of iterations may be performed during the reconstruction, such that during each of the iterations, a reconstructed image may be generated. When a termination criterion is satisfied, for example, the difference between the reconstructed image from the current iteration and the preceding iteration is below a certain threshold, the iteration may terminate. A reconstructed image may be proceeded to perform image correction at step 509. During the image correction, the noise in the reconstructed image may be further reduced. Moreover, step 508 may also include a process to enhance the contrast of the reconstructed image.

It should be noted that the description of the scanning system is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure. For example, the initialization may be performed by executing instructions stored in a storage unit, or a user may control the initialization and set the parameters manually. The working condition and/or sensitivity of detector cells may also be taken in account when the scanning system is initialized and/or the parameters of interest is adjusted.

Figure 6:
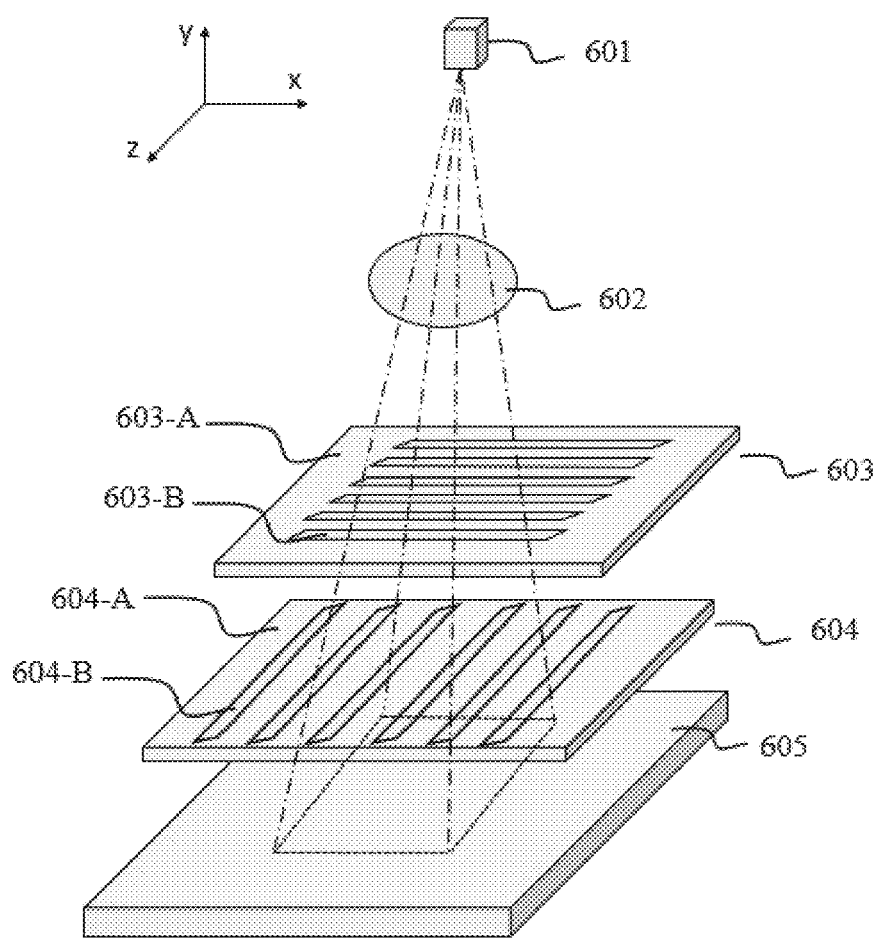
FIG. 6 is a 3D schematic of an X-ray imaging scanner according to some embodiments of the present disclosure.

FIG. 6 is a 3D schematic of an X-ray imaging scanner with two grids set before the X-ray detector. It should be noted that the configuration described in the figure is merely for exemplary purposes, and is not intended to be limiting.

As shown in FIG. 6, an X-ray generating unit 601 may emit radiation toward, for example, an object 602, a grid (for example, a first grid 603, a second grid 604, etc.), an X-ray detector 605, or the like, or a combination thereof. The radiation traversing the object 602 may be detected by the X-ray detector 605. Because of the first grid 603 and the second grid 604 located between the object 602 and the X-ray detector 605, part of the radiation may be blocked and/or absorbed. The shape of the X-ray beams emitted by the X-ray generating unit 601 may be a line, a narrow pencil, a narrow fan, a fan, a cone, a wedge, or the like, or an irregular shape, or any combination thereof. The X-ray generating unit 601 may include a focal spot where the radiation is emitted. In some embodiments, the focal spot of the radiation including, for example, X-ray beams, may be at a fixed position inside the X-ray generator or the X-ray generating unit 601. In some embodiments, the focal spot of the radiation including, for example, X-ray beams, may be movable inside the X-ray generator or the X-ray generating unit 601. The trajectory of the focal spot may be continuous or discrete. In some embodiments, the continuous trajectory may be a line, a sine curve, a sawtooth wave, or other regular or other irregular shape. In some embodiments, for the discrete trajectory, the number of the positions of the focal spot may be, for example, two, three, four, five, or more. The positions may be in a line, in a plane, or in a three-dimensional (3D) space. In some embodiments, the interval between each two positions may be equivalent or not. In some embodiments, the shape formed by these positions may be a triangle, isosceles or not. In some embodiments, the shape formed by these positions may be a quadrangle, including, a rectangle, a diamond, or any shapes with four edges. In some embodiments, the shape formed by these positions may be a circular, an ellipse. In some other embodiments, the shape formed by these positions may be a three dimensional figure, including a solid, a sphere, or any shapes regular or irregular. The speed and the movement of the focal spot may be controlled by the X-ray controller 410 according to the demands including, the spatial resolution, the position of the grids set in the system, or the like, or a combination thereof. The X-ray controller 410 may supply a control parameter to the X-ray generating unit, including, a voltage, a current, an electric field, a magnetic field, or the like, or any combination thereof. In some embodiments, the control parameter may be constant or variable. In some embodiments, the variation may be continuous or a step change, and the step may be equal or unequal. With the movement of the focal spot of the X-ray beam, the active area of receiving radiation for a detector cell of an X-ray detector may be changed. In some embodiments, the active area of receiving radiation for each detector cell may be changed. In some embodiments, the active area of receiving radiation for part of the detector cells may be changed.

As shown in FIG. 6, the first grid 603 and the second grid 604 set between the target 602 and the X-ray detector 605 may be configured to block and/or absorb some radiation traversing the target 602 and the radiations directly from the X-ray generating unit 601. It should be noted that the grids 603 and 604 are merely for exemplary purposes, and is not intended to be limiting. In some embodiments, there may be one or more grids set between the target 602 and the X-ray detector 605. In some embodiments, there may be one or more collimators (not shown in FIG. 6)) set between the X-ray generating unit 601 and the target 602. The shape of the grids may be flat, arc-shaped, circular, or the like, or any combination thereof, and the first grid 603 and the second grid 604 may be the same or different in configuration. As illustrated in FIG. 6, the first grid 603 may include a plurality of radiation absorbing portions 603-A and a plurality of radiation transmitting portions 603-B. The second grid 604 may include a plurality of radiation absorbing portions 604-A and a plurality of radiation transmitting portions 604-B. The first grid 603 may be parallel to the second grid 604. The radiation transmitting portions 603-B may be parallel with each other, extending along the X-direction. The radiation transmitting portions 604-B may also be parallel with each other, extending along the Z-direction. As described elsewhere in the disclosure, at least one shielding device may be used in combination with the first grid 603 and/or the second grid 604 so as to adjustably block the radiation from the X-ray source. The shielding device may be arranged in different manners. For example, the shielding device may be placed between the detector and the grid. For another example, the shielding device may be placed between the detector and the second grid 604. For still another example, the shielding device may be placed between the first grid 603 and the second grid 604. In a further example, a plurality of shielding devices may be placed in different positions with respect to different grids. Embodiments of the shielding device are illustrated in FIG. 13-A and FIG. 13-B and the description thereof.

It should be noted that the above description about the grids is merely an example, and not intended to limit the scope of the present disclosure. For persons having ordinary skills in the art, multiple variations and modifications may be made under the teachings of the present disclosure. For example, the shape of the radiation transmitting portions 603-B and/or the radiation transmitting portions 604-B may be regular or irregular. In some embodiments, the radiation transmitting portions 603-B and/or the radiation transmitting portions 604-B may be uniform in shape. In some other embodiments, a first part of the radiation transmitting portions 603-B and/or the radiation transmitting portions 604-B is same in shape, a second part of the radiation transmitting portions 603-B and/or the radiation transmitting portions 604-B is in a shape different from those of the first part. The width and the length of the radiation transmitting portions 603-B and/or the radiation transmitting portions 604-B may be arbitrary. In some embodiments, the grid pitch of the radiation transmitting portions 603-B and the radiation transmitting portions 604-B may be the same or different. For either grid, the pitches of the radiation transmitting portions may be uniform, or partially uniform, or non-uniform.

The radiation absorbing portions 603-A and/or 604-A may be formed with highly absorbing material with large density or heavy nuclei atoms. In some embodiments, the absorbing material of the radiation absorbing portions 603-A may be same with the material of the radiation absorbing portions 604-A. In some embodiments, the absorbing material of the radiation absorbing portions 603-A may be different from the material of the radiation absorbing portions 604-A. Merely by way of example, the absorbing materials may be lead, gold, tungsten, depleted uranium, thorium, barium sulfate, tantalum, iridium, osmium, or the like, or any combination thereof. The radiation transmitting portions 603-B and 604-B may include any material whose absorbability is smaller than the absorbing materials. The radiation transmitting portions 603-B and 604-B may be filled with materials including gas, inorganic material, organic material, or the like, or any combination thereof. For example, the gas may include oxygen, nitrogen, carbon dioxide, hydrogen, air, or the like, or any combination thereof. Exemplary inorganic material may include silicon, carbon fiber, glass, etc. Exemplary organic material may include plastic, rubber, etc. In some embodiments, the material of the radiation transmitting portion 603-B may be same with the material of the radiation transmitting portion 604-B. In some other embodiments, the material of the radiation transmitting portion 603-B may be different from the material of the radiation transmitting portion 604-B. Note that the above embodiments are purely provided for illustration, the present disclosure is not limited to these embodiments. Persons having ordinary skills in the art may make some variations, deformations and/or modifications without any creativity according to the present disclosure. In some embodiments, the grids 603 and 604 may also be incorporated with some components such as electrodes. The variations, deformations and/or modifications are not departing from the spirits of the present disclosure.

The grids 603 and 604 may be controlled to move by the grid controller 430 of the control module 220. The control factor may be a voltage, a current, an electric field, a magnetic field, or the like, or any combination thereof. With the movement of the grids, the active area of receiving radiation for a detector cell of an X-ray detector may be changed. For example, when the first grid 603 moves along the Z-direction when the position of the second grid 604 is fixed, the active area of receiving the radiation on a detector cell along the Z-direction may be changed. For another example, when the second grid 604 moves along the X-direction when the position of the first grid 603 is fixed, the active area of receiving the radiation on a detector cell along the X-direction may be changed. For another example, when the first grid 603 moves along the Z-direction and the second grid 604 moves along the X-direction, the active area of receiving the radiation on a detector cell along the X-direction and Z-direction may both be changed. It should be not that, the above description about the movement of the grids is merely an example, and not intend to be limiting. In some embodiments, the grid 603 and the grid 604 may move along a same direction. The moving distance for the grid 603 and/or the grid 604 may be arbitrary. In some embodiments, the grid 603 and the grid 604 may tilt about a certain axis, such as the x axis, y axis, or z axis. The tilting of the first grid 603 and the second grid 604 may be about the same or different directions. In some other embodiments, there may be only one grid. The tilting and/or movement of the grid may still result in changed active area of receiving radiation on a detector cell. In still some other embodiments, there may be more than two grids. The combinational tilting and/or movement of each grid may also result in changed active area of receiving radiation on a detector cell. When the active area of receiving radiation on a detector cell is changed, the special resolution may be changed. The structure of the grids described above is aimed at a detector cell, but it should be noted that it may also be suitable for a whole detector or part of a whole detector.

It should be noted that the above description of the grids and relative motions is merely provided for the purposes of illustration, and not intended to limit the scope of the present disclosure. For persons having ordinary skills in the art, multiple variations and modifications may be made under the teachings of the present disclosure. In some embodiments, the grids may be within a same plane. In some embodiments, the grids may be arranged contacting directly with each other. For example, the grids may be arranged along the X-direction, the Y-direction, or the Z-direction. In some embodiments, the grids may be spaced from each other by a certain distance. In some embodiments, a grid and a detector may attach to each other or be spaced from each other by a certain distance. In some embodiments, the grids may be arranged parallel to a detector. In some embodiments, the grids may be arranged at an angle to the detector, and the angle may be adjustable from 0° to 360°. In some embodiments, the grids may be arranged in parallel with other grids or be arranged at angle to one or more other grids, and the angle may be adjustable from 0° to 360°.

Figure 7:
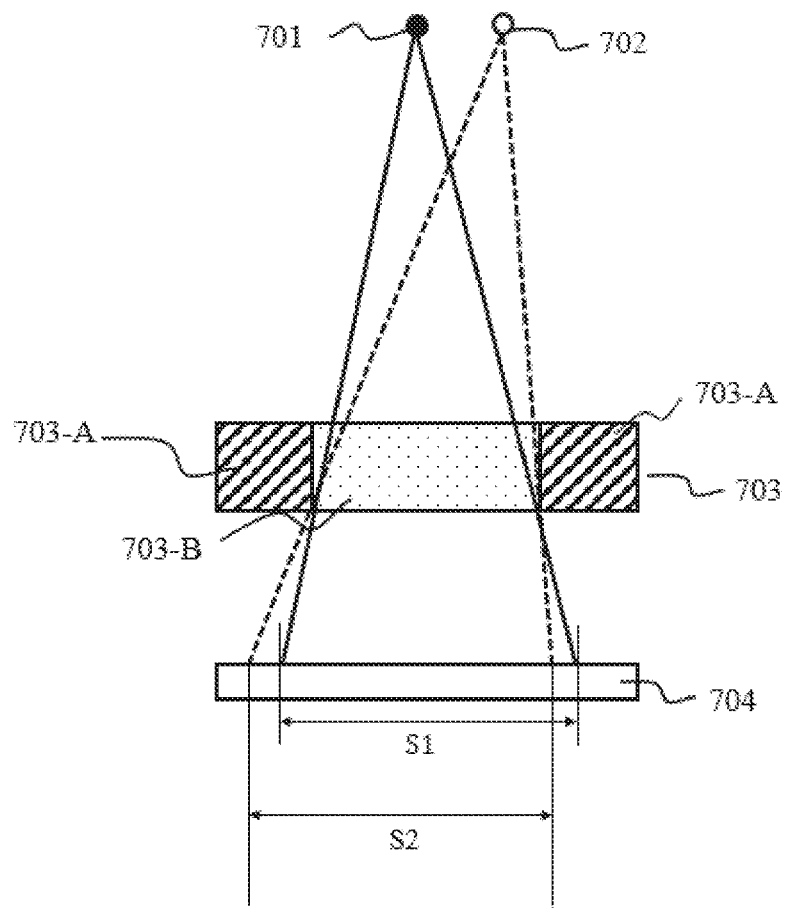
FIG. 7 is a schematic sectional view of the effect of a flying focal spot on the active area of a detector cell according to some embodiments of the present disclosure.

FIG. 7 shows a schematic sectional view of the effect of a flying focal spot on the active area of a detector cell. In the figure, the number 701 and 702 may represent two positions of a focal spot of the radiation beam inside an X-ray generating unit, the number 703 may represent a grid including radiation absorbing portions 703-A and a radiation transmitting portion 703-B. The radiation emitted from the points 701 and 702 may project on a detector cell 704 through the radiation transmitting portion 703-B of the grid 703. It should be noted that the structure showed in this figure is merely for the purposes of describing conveniently, and is not intended to be limiting. For persons having ordinary skills in the art, the number of the focal spot and that of the grid may be varied arbitrarily according to some embodiments of the present disclosure, and the relative position of the two focal spot may change according to some embodiments of the present disclosure.

As shown in FIG. 7, when the focal spot of the radiation beams is at point 701, the width of the region of receiving the radiation is S1. When the focal spot of the radiation beams moves to point 702 under the control of, for example, the X-ray controller, the width of the region of receiving the radiation is S2 that may be different from the width S1. The difference in S1 and S2 may result in different active areas that may receive the radiation on the detector cell 704. The point 702 may be anywhere different from the point 701. In some embodiments, the point 702 may be on the left side of the point 701, on the right side of the point 701, above the point 701, under the point 701, or the like, or a combination thereof. For persons having ordinary skills in the art, it should be understood that when the point 701 and the point 702 do not coincide exactly, the width S1 and S2 may be different.

Beside, when the focal spot of the radiation beams is fixed, the change of the location of the grid 703 may result in a different active area on a detector cell. In some embodiments, the grid 703 may move a distance towards the focal spot 701 or the detector cell 704 according to different demands including, e.g., a desired spatial resolution, the size of the X-ray imaging scanner, the whole size of the detector and the size of a detector cell, or the like, or any combination thereof. There may be other factors that may influence the active area of a detector cell, such as, the width of the radiation transmitting portion 703-B, the thickness of the radiation transmitting portion 703-B, the shape of the radiation transmitting portion 703-B, the distance between the grid 703 and the detector cell 704, the distance between the focal spot of the radiation beam and the grid 703, the angle formed by the grid 703 and the detector cell 704, the shape of the radiation beam, the motion speed of the focal spot and/or the grids, or the like, or any combination thereof. In some embodiments, the shape of sectional view of the radiation transmitting portion 703-B may be trapezoid, taper, triangle, or other shapes such as a handstand T shape.

Those skilled in the art should understand that the above embodiments are only utilized to describe the present disclosure. There are many modifications and variations to the present disclosure without departing from the spirits of the present disclosure. For example, there may be two or more grids arranged before the detector cell 704, and the active area of a detector cell 704 may be determined by all the grids arranged.

Figure 8:
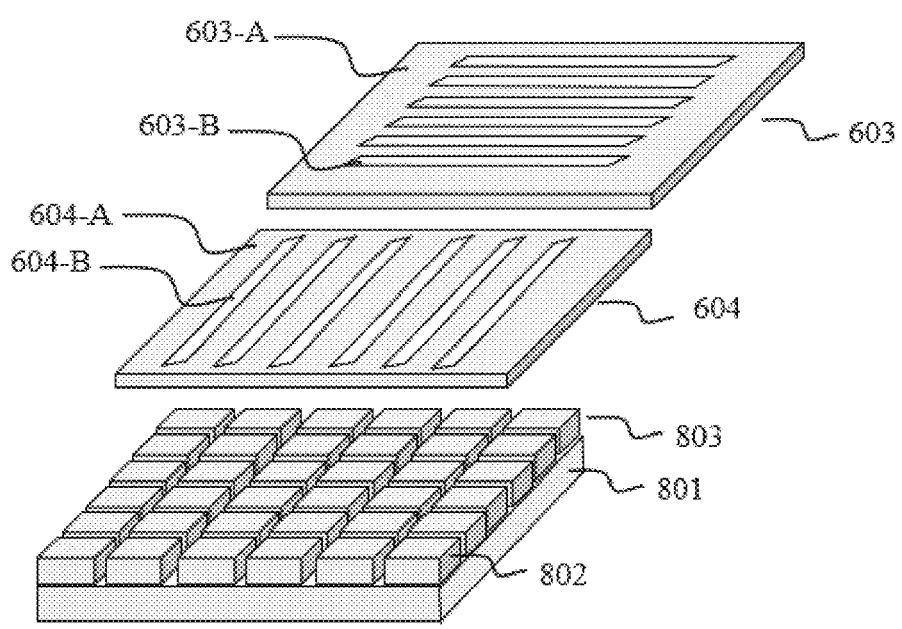
FIG. 8 is a schematic view of a detector array according to some embodiments of the present disclosure.

FIG. 8 shows a schematic view of a combination of grids and a detector. The detector 803 may include a plurality of detector cells 802 supported by a substrate 801. In some embodiments, a detector cell may include one or more scintillator element and one or more photodetector element. The scintillator element may include a material that may absorb ionizing radiation and/or emit a fraction of the absorbed energy in the form of light. Any scintillator may include a material with at least one of the following features including, for example, a high detective efficiency, high conversion efficiency, low absorption, a wide linear range, strong resistance to interference, or the like, or a combination thereof. The photodetector element in the present disclosure may be a photoelectric conversion element that may firstly detect an optical signal and then convert the optical signal into an electrical signal including, e.g., an electrical current, an electrical voltage, and/or other electrical phenomena. In some embodiments, the thickness of the detector cell 802 may be varied. The size of the detector cell 802 may be varied one or more conditions including, for example, spatial resolution, sensitivity, stability, the size of the detector or the like, or any combination thereof. The shape of the detector cell 802 may be circular, oval, rectangular, or the like, or any combination thereof. The detector cell may be arranged regularly, or irregularly on the substrate 801. In some embodiments, the working conditions of each detector cell 802 may be controlled independently by the control module 220.

The substrate 801 may be a solid substance providing a support for the detector 803. The size of the substrate 801 may be varied according to the size of the detector 803. The thickness of the substrate 801 may be varied arbitrarily and not limited here. The overall shape of the substrate 801 may be planar, arc-shaped, or any other shaped substrate in accordance to the different shapes of the X-ray detector 300. Each part of the substrate 801 may be circular, oval, rectangular, or the like, or any combination thereof. The substrate 801 may be arranged regularly, or irregularly. The substrate 801 may include, for example, a semiconducting material, an electrically insulating material, or the like, or a combination thereof. In some embodiments, the semiconducting material may include an elementary substance or a compound. The elementary substance may include silicon, germanium, carbon, tin, or the like. The compound may include silicon dioxide, silicon nitride, silicon carbide, aluminum oxide, sapphire, germanium, gallium arsenide (GaAs), an alloy of silicon and germanium, indium phosphide (InP), poly (3-hexylthiophene), poly (p-phenylene vinylene), polyacetylene, or the like, or their derivatives, or any combination thereof. In some embodiments, the insulating materials may include glass, porcelain, paper, polymers, plastics, or the like, or any combination thereof. Those skilled in the art should understand that the above embodiments are only utilized to describe the present disclosure. There may be many modifications and variations to the present disclosure without departing form the spirits of the present disclosure. For example, the substrate element may be small chips to minimize the size of the X-ray detector. For another example, the X-ray detector may also be an assembly of scintillator elements, photovoltaic conversion elements, chips and other components. For still another example, the substrate or chip may be omitted in some embodiments. Similar modifications and variations are still within the scope of the present disclosure described above.

As shown in FIG. 8, the first grid 603 and the second grid 604 may be arranged in front of the detector 803. The first grid 603 may be parallel to the second grid 604. The radiation transmitting portions 603-B extending along the X-direction on the first grid 603 may be parallel with each other. The radiation transmitting portions 604-B extending along the Z-direction on the second grid 604 may be parallel with each other. It should be noted the above description about the grids is merely an example, and not intended to limit the scope of the present disclosure. For persons having ordinary skills in the art, multiple variations and modifications may be made under the teachings of the present disclosure. In some embodiments, the shape of the radiation transmitting portions 603-B and the radiation transmitting portions 604-B may be regular, e.g., a rectangle, a trapezia, a parallelogram. The width and/or the length of the radiation transmitting portions 603-B and the radiation transmitting portions 604-B may be arbitrary. In some embodiments, the grid pitch of the radiation transmitting portions 603-B and the transmitting portions 604-B may be the same or different. For the first grid and/or the second grid, the grid pitches of the radiation transmitting portions may be uniform, partially uniform, or non-uniform. For example, half of the radiation transmitting portions may have a first grid pitch, and the remaining half of the radiation transmitting portions may have another grid pitch which may be different from the first grid pitch. For still another example, all the distances between two neighbor radiation transmitting portions may be different. In some embodiments, the radiation transmitting portions 603-B may extend in the same direction with the radiation transmitting portions 604-B. In some embodiments, the radiation transmitting portions 603-B may extend in a different direction with the radiation transmitting portions 604-B. For example, the extending direction of the radiation transmitting portions 603-B and the extending direction of the radiation transmitting portions 604-B may be orthogonal. The modifications and variations are still within the scope of the present disclosure described above. In some embodiments, a detector cell may correspond to one or more radiation transmitting portion(s) from a grid. In some embodiments, a detector cell may correspond to one or more radiation transmitting portion(s) from more than one grids.

The grid 603 and grid 604 may be controlled to move by the grid controller 430 in the control module 220. The control factor may be a voltage, a current, an electric field, a magnetic field, or the like, or any combination thereof.

Figure 9:
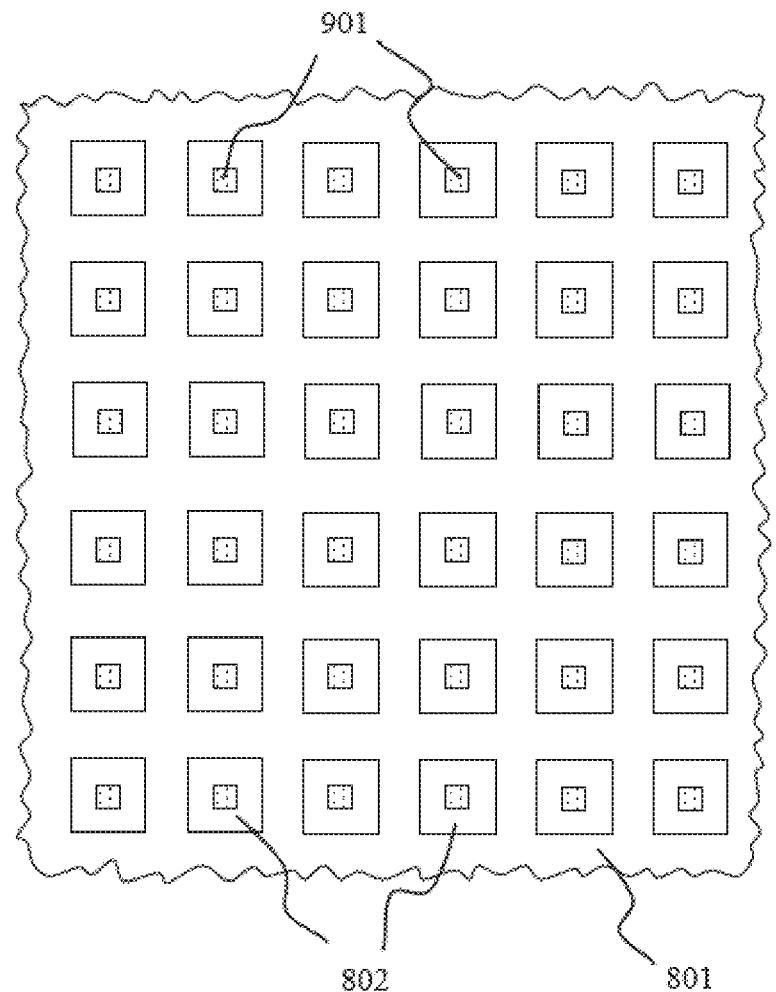
FIG. 9 is a schematic view of the active areas of detector cells according to some embodiments of the present disclosure.

FIG. 9 is a schematic view of active areas of detector cells on a detector. It should be noted that the arrangement of the detector cells is merely for illustration purposes, and is not intended to be limiting. In some embodiments, the gaps among the detector cells may be filled with some materials to absorbed and/or block the X-rays to prevent the chips from being influenced.

As illustrated in the figure, each detector cell 802 may have an active area 901, which may be adjustable according to some considerations including, e.g., the spatial resolution, the system noise, one or more other types of noises, or the like, or a combination thereof. The active area 901 may be determined by, for example, the geometrical relationship of the focal spot of the radiation beam and/or the grids between the target and the detector. The position of the active area 901 may move and/or the scale of the active area 901 may change when the focal spot of the radiation beam moves, and/or the position of the grids changes.

It should be noted that the above description of the active area is merely provided for the purposes of illustration, and not intended to limit the scope of the present disclosure. For persons having ordinary skills in the art, multiple variations and modifications may be made under the teachings of the present disclosure. For example, the shape of the active area may be a triangle, quadrangle, including, a rectangle, a diamond, or any shapes with four edges. In some embodiments, the shape formed by these positions may be a circular, an ellipse. In some embodiments, the shape of the active area may be an irregular shape. In some embodiments, there may be several active areas for one detector cell and the active areas may have a same, or different, shape(s). For example, there may be two or more rectangular active areas for a detector cell. In some embodiments, the position of the active areas may be anywhere of a detector cell.

Figure 10:
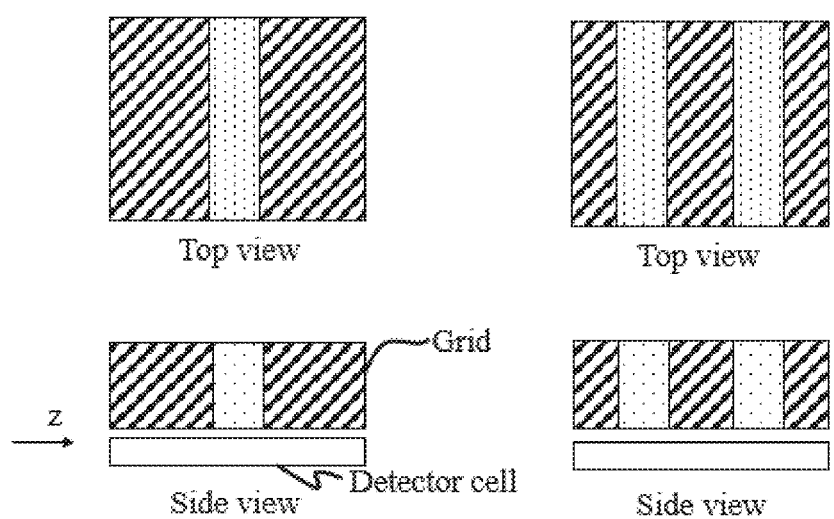
FIG. 10-A and FIG. 10-B are schematic diagrams showing an exemplary arrangement of the grid and the detector cell according to some embodiments of the present disclosure.

FIG. 10-A and FIG. 10-B are schematic diagrams showing an exemplary arrangement of the grid and the detector cell according to some embodiments of the present disclosure. To be convenient for description, only one detector cell and one grid used for adjusting the active area of the detector cell are shown in FIG. 10-A. It should be noted that a detector including a plurality of detector cells may be used for acquiring X-ray signals (see FIG. 8). And it should be noted that at least one grid may be used for adjusting the active area of the detector cells (e.g., two grids may be used, see FIG. 8). As illustrated in FIG. 8, a grid may include one or more radiation transmitting portions 603-B (or 604-B) and one or more radiation absorbing portions 603-A (or 604-A). X-rays may be transmitted through the radiation transmitting portions while absorbed by the radiation absorbing portions. The radiation transmitting portion may be an empty gap, or may be filled with certain medium. Exemplary medium may include inorganic material, organic material, or the like, or any combination thereof. Exemplary inorganic material may include silicon, carbon fiber, glass, or the like, or a combination thereof. Exemplary organic material may include plastic, rubber, or the like, or a combination thereof.

A radiation transmitting portion, or referred to as a radiation transmitting section, may be used for adjusting the active area of a detector cell. The active area of a detector cell may receive radiation from a radiation source that passes through at least one of a plurality of radiation transmitting sections of a grid. At least one of the radiation transmitting section may include at least one transmitting part located above a detector cell. The active area may correspond to the radiation transmitting section or portion in a grid located above the detector cell. The dimension of the active area of a detector cell may be comparable to the dimension of the detector cell. For example, assume the dimension of the detector cell is 1×1 mm$^2$, the dimension of the active area corresponding to the transmitting part located above the detector cell may be less than 1 mm$^2$, such as, from $9/10$ mm$^2$ to 1 mm$^2$, or from $4/5$ mm$^2$ to $9/10$ mm$^2$, or from $3/4$ mm$^2$ to $4/5$ mm$^2$, or from $1/2$ mm$^2$ to $3/4$ mm$^2$, or from $2/5$ mm$^2$ to $1/2$ mm$^2$, or from $1/3$ mm$^2$ to $1/3$ mm$^2$, or from $1/4$ mm$^2$ to $1/3$ mm$^2$, or from $1/5$ mm$^2$ to $1/4$ mm$^2$, or from $1/6$ mm$^2$ to $1/5$ mm$^2$, or below $1/6$ mm$^2$, or the like. In some embodiments, the dimension of the detector cell may be P mm$^2$ other than 1×1 mm$^2$, and the dimension of the active area corresponding to the transmitting part located above the detector cell may be b*P. The value of the factor b may be any number in the range (x, 1), such as $1/2$, $1/3$, $1/4$, $1/5$, $1/6$, $1/10$, $1/20$, $1/50$, $1/100$, or the like. As used herein, the variable x may be set by the system according to a default setting, or may be set by an operator, or may be set according to requirements of signal acquisition process. The value of x may be between 0 and 1. In some embodiments, the variable x may be set to be equal to or greater than 0.01, or 0.05, or 0.1, or 0.2, or 0.3, or 0.4, or 0.5, or 0.6, or 0.7, or 0.8.

Merely by way of example, the radiation transmitting portions may be arranged along X-direction or along Z-direction to form a stripe pattern (e.g., the shape of the radiation transmitting portion is rectangle). In some embodiments, the shape of the radiation transmitting portion may be square, triangle, circle, oval, polygon, irregular shape, or the like, or a combination thereof. The area ratio of the radiation transmitting portions and the radiation absorbing portions may be a fixed value, or may be adjustable under different conditions. Similarly, the grid pitches among the radiation transmitting portions may be a fixed value, or may be adjustable under different conditions. Merely by way of example, a doctor or an operator other than the doctor (e.g., a health-care worker) may manually adjust the grid pitches according to requirements of signal acquisition process or according to requirements of image quality (e.g., resolution, S/N (signal/noise), amplification factor, or the like, or a combination thereof.). For another example, the operator may adjust the grid pitches based on instructions inputted by the doctor or a related operator, or based on system default, or based on options regarding preset parameters (e.g., different conditions correspond to different parameters). The preset parameters may include signal acquisition speed, size of detector pixel, emitting voltage, emitting current, temperature, or the like, or a combination thereof.

FIG. 10-A provides one example regarding the adjusting of active area of a detector cell according to some embodiments of the present disclosure. A top view and a side view from Z-direction are shown. As illustrated, the region filled with slash lines represents the radiation absorbing portions of the grid, the region filled with points represents a transmitting part of a radiation transmitting portion of the grid, and the region with no fill represents the detector cell. In this example, the shape of the transmitting part of the radiation transmitting portions may be rectangle as illustrated in FIG. 10-A. During an X-ray image acquisition process, based the system default or instructions inputted by an operator, the grid may be controlled to move toward the detector cell or the focal spot. The controlling may be performed by the control module 220, or may be performed by the grid controller 430, or may be performed by any module or unit integrated in the system that may be configured for controlling positions or arrangements of components of the system. For purposes to be illustrative, a radiation transmitting portion or a transmitting part of a radiation transmitting portion may be arranged on the middle part of the detector cell, but it should be noted that this illustration will not limit the scope of the present disclosure. It may be seen from the top view and the side view that due to the existence of the radiation transmitting portion and the radiation absorbing portion of the grid, the active area of the detector cell is reduced. The active area of the detector cell may be adjusted by adjusting the radiation transmitting portion's shape, size, position, arrangement, or the like, or a combination thereof.

The description of the arrangements of the grid and the detector cell are intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, other than the situation illustrated in FIG. 10-A, the size or shape of the radiation transmitting portion may be changed, thus the active area of the detector cell or the size of the transmitting part of the radiation transmitting portion may be accordingly reduced. In some embodiments, assume that the size of a detector cell illustrated in FIG. 10-A is S mm$^2$, the size of the radiation transmitting portion or the size of the transmitting part of the radiation transmitting portion may be reduced to a*S mm$^2$ according to the requirements of signal acquisition process. The value of the factor a may be any number in the range of (0, 1) (e.g., $1/2$, $1/3$, $1/4$, $1/5$, $1/6$, $1/10$, $1/20$, $1/50$, $1/100$, etc.). Similarly the size of the radiation transmitting portion or the transmitting part of the radiation transmitting portion may be enlarged accordingly.

FIG. 10-B provides another example regarding the adjusting of the active area of the detector cell according to some embodiments of the present disclosure. It may be seen from the top view that two transmitting parts 1002 of the radiation transmitting portion of the grid are arranged above the detector cell. Similarly the active area of the detector cell is reduced due to the existence of the radiation transmitting portion and the radiation absorbing portion. Referring back to FIG. 10-A, the active area of the detector cell may be adjusted or may be controlled by adjusting one or more parameters of the radiation transmitting portions. The parameters may include the shape, the size, the grid pitch among the radiation transmitting portions, the amount of the radiation transmitting portions, the position of the grid, the filling material of the radiation transmitting portions, or the like, or a combination thereof. As shown in FIG. 10-B, two transmitting parts of the radiation transmitting portions are arranged, it should be noted that the arrangement is only for purpose of illustration, and not intended to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, other than the two exemplary arrangements, one, three or more transmitting parts of the radiation transmitting portions may be arranged above the detector cell. Thus the active area of the detector cell may be adjusted accurately and continuously.

Figure 11:
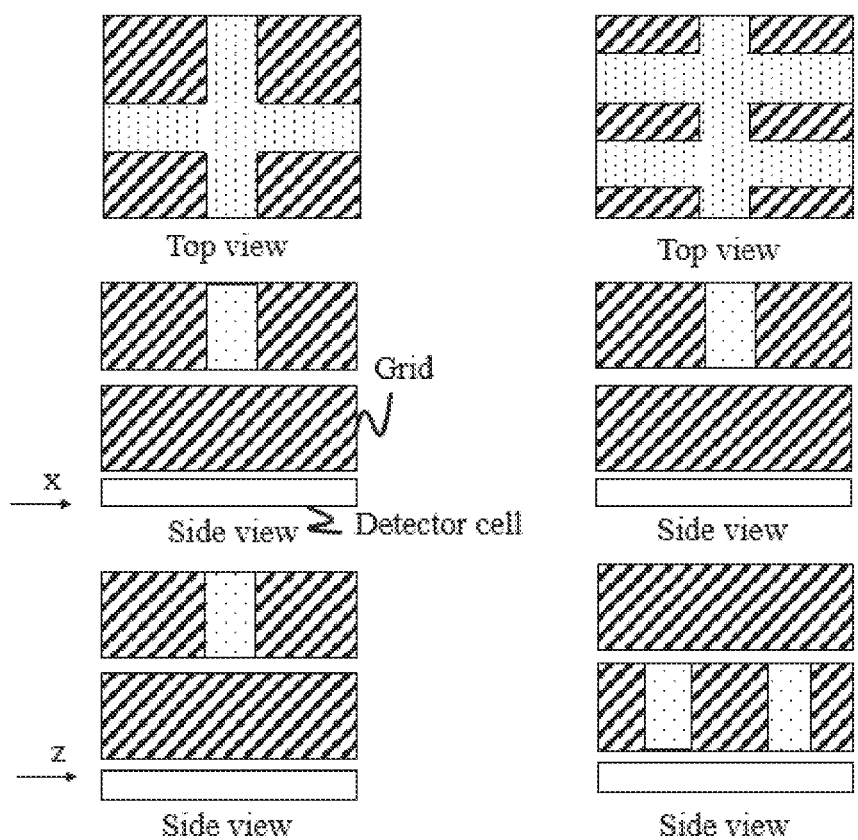
FIG. 11-A and FIG. 11-B are schematic diagrams showing another exemplary arrangement of the grid and the detector cell according to some embodiments of the present disclosure.

FIG. 11-A and FIG. 11-B are schematic diagrams showing another exemplary arrangement of the grid and the detector cell according to some embodiments of the present disclosure. Two grids are arranged above the detector array used for adjusting the active areas of the detector cells. To be convenient for illustration, only one detector cell is shown. According to this embodiment, two grids may be configured for adjusting the active areas of the detector cells illustrated in FIG. 8. In some embodiments, the two girds may be configured orthogonally, or may be arranged at a certain angle with each other. The angle may be 10°, 15°, 30°, 45°, 60°, or the like. The active area of the detector cell may be adjusted based on the change of the angle. The change of the angle may be performed based on system default, or may be based on instructions inputted by a doctor or an operator other than the doctor, or may be based on instructions or preset conditions loaded from the server. The change of the angle may be performed by the control module 220, or may be performed by the grid controller 430, or may be performed by any module or unit integrated in the system that may be used for controlling positions or arrangements of components of the system. The type of the two grids may be the same or may be different.

FIG. 11-A provides one example regarding the adjustment of the active area of a detector cell according to some embodiments of the present disclosure. A top view, a side view from X-direction, and a side view from the Z-direction are shown. In this example, it may be seen from the top view that a "+" radiation transmitting region is generated by two orthometric grids. In some embodiments, the two grids may be arranged at a certain angle, and thus the radiation overlapping area may be adjusted by tilting one or both grids. The size of the "+" radiation transmitting region may be changed by changing the size or the shape of the radiation transmitting portions of the two grids. Thus the active pixels in the X-direction, the Z-direction, and the XY-plane may be adjusted and controlled. It should be noted that the active area may be determined by both the radiation transmitting regions of the grid(s) and the position of the focal spot.

FIG. 11-B provides another example regarding the adjusting of active area of a detector cell according to some embodiments of the present disclosure. Similarly, a top view, a side view from the X-direction, and side view from the X-direction are shown. In this example, a radiation transmitting region illustrated in FIG. 11-B is generated by two orthometric grids. Name the upper gird as the first grid and name the under grid as the second gird (see FIG. 8). In the example, the grid pitches among the radiation transmitting portions of the two grids may be different. It may be seen from the side view from the X-direction that one radiation transmitting portion of the first grid is arranged above the detector cell, and no radiation transmitting portion of the second grid is arranged on the detector cell. It may be seen from the side view from the Z-direction that two radiation transmitting portions of the second grid are arranged above the detector cell, and no radiation transmitting portion of the first grid is arranged on the detector cell. This description is only for purpose of illustration, more than one radiation transmitting portions of the first grid and other than two radiation transmitting portions of the second grid may be arranged above the detector cell. The radiation transmitting region of the detector cell may be adjusted and controlled by the two grids under different conditions.

Figure 12:
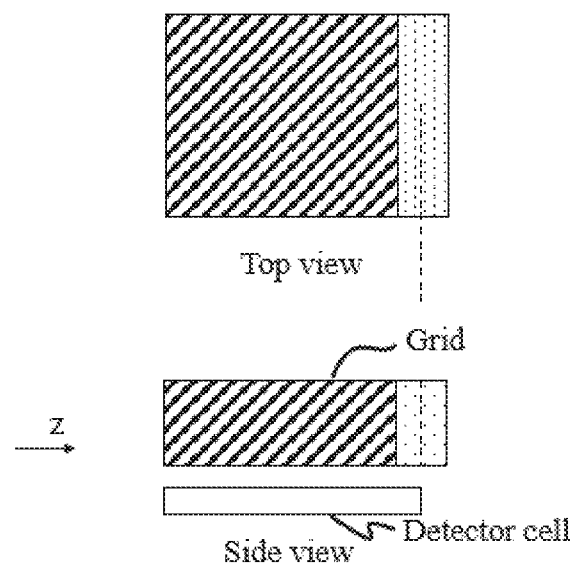
FIG. 12 is a schematic diagram showing another exemplary arrangement of the grid and the detector cell according to some embodiments of the present disclosure.

FIG. 12 is a schematic diagram showing another exemplary arrangement of the grid and the detector cell according to some embodiments of the present disclosure. As illustrated, the radiation transmitting portion of the grid is arranged on the edge of the detector cell. Similar to the situation that the radiation transmitting portion of the grid arranged in the middle of the detector cell, the active area of the detector cell may be reduced by the existence of the grid. For example, ½ of the transmitting part of the radiation transmitting portion of the grid is located above the detector cell, the active area of the detector cell is reduced as ½ of the area of the transmitting part of the radiation transmitting portion. In a further example, the grid may be caused to move along the X-direction or along the Z-direction, while approaching the edge of detector cell, the radiation transmitting region above the detector cell may vary in real time. According to desired image quality or signal acquisition requirements of different organs of the object, the gird may be controlled to move under a certain speed or along a certain route. In still a further example, there may be two or more grids. The grids may be controlled together or may be controlled independently. The moving of the grids may include translation, tilt, or the like, or a combination thereof. The adjusting of the active area of a detector cell may be in real time, or may be pre-set before the X-ray image acquisition process commences, or may be performed when needed.

The description of the arrangements of the grid and the detector cell are intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, parameters regarding the adjusting of the active area of a detector cell may be controlled in real time and may be controlled independently. The parameters may include but not limited to, the size or shape of the radiation transmitting portion, the moving speed of the grids, the number of the grids, the angle between the grids, or the like, or a combination thereof.

FIG. 13-A and FIG. 13-B are schematic diagrams showing exemplary arrangements of a grid, a shielding device, and a detector cell according to some embodiments of the present disclosure. For simplicity, only a portion of a grid, a part of a shielding device, and a detector cell are shown in FIG. 13-A and FIG. 13-B. It is for illustration purposes and not intended to limit the scope of the present disclosure. It is understood that an imaging system may include more than one grids, that a grid may include more than one shielding device, and that an imaging system may include more than one detector cells.

In FIG. 13-A, a top view from the Y-direction is shown. A plate of the shielding device 1302 may be placed on or above the grid 1301. In some embodiments, the shielding device 1302 and the grid 1301 may physically contact or be in direct contact with each other. In some embodiments, the shielding device 1302 and the grid 1301 may be spaced apart from each other by a distance. In some embodiments, the plate of the shielding device 1302 may contact the radiation absorbing portion 1301-A of the grid 1301. In some embodiments, the plate of the shielding device 1302 may contact the radiation transmitting portion 1301-B of the grid 1301. In some embodiments, the shielding device 1302, or a portion thereof, may be parallel to the grid 1301. In some embodiments, the shielding device 1302, or a portion thereof, may be placed at an angle of inclination with respect to the grid 1301. The angle may be adjustable from 0° to 360°.

In FIG. 13-B, the radiation absorbing portion 1301-A may be filled with materials including gas, therefore, the shielding device 1302 may be place on a side of the radiation absorbing portion 1301-A of the grid 1301 as shown in FIG. 13-B. It should be noted that the position of the shielding device shown in the figure is merely an exemplary example, and not intend to be limiting. In some embodiments, the shielding device 1302 may be any position in the radiation absorbing portion 1301-A. In some embodiments, the shielding device 1302 may be placed apart from the grid with a distance. For the purposes of describing conveniently, FIG. 13-B may show an exemplary example.

In FIG. 13-B, a side view from Z-direction of the arrangement is shown. A plate of the shielding device 1302 is illustrated in HG, 13-B. The plate of the shielding device 1302 may be movably attached to a side of the radiation absorbing portion 1301-A at a connecting point 1304. The plate of the shielding device 1302 may swing around the connecting point 1304 by any angle between, for example, 0° to 90°, or 0° to 180°, or 0° to 270°. The trajectory of one end of the plate in the shielding device 1302 may form an arc with a radius. When the plate of the shielding device 1302 is at different positions, the active area of the detector cell 1303 may be different. The different length or width of the plate of the shielding device 1302 (the radius shown in FIG. 13-B) may also result in different active area of the detector cell 1303.

The shape of the shielding device 1302 may be regular or irregular. Merely by way of example, the shielding device 1302 may be one or more plates with dimensions including, for example, a length, a width, a height, etc. The length and the width of a plate of the shielding device 1302 may be comparable to a radiation transmission section portion 1301-B of the grid 1301.

The working condition or a position of the shielding device 1302, or a portion there of (for example, a plate of the shielding device 1302) may include an extended position, a partially extended position, and a contracted position. As used herein, an extended position of the shielding device 1302, or a portion there of, may be one at which the shielding device 1302, or a portion thereof, completely blocks or absorbs one or more radiation transmission section portions 1301-B of the grid 1301, and no area(s) of one or more radiation transmission section portions 1301-B of the grid 1301 may be available for passage of radiation. As used herein, a partially extended position of the shielding device 1302, or a portion there of, may be one at which the shielding device 1302, or a portion thereof, partially blocks one or more radiation transmission section portions 1301-B of the grid 1301, and partial area(s) of one or more radiation transmission section portions 1301-B of the grid 1301 may be available for passage of radiation. As used herein, a contracted position of the shielding device 1302, or a portion there of, may be one at which the shielding device 1302, or a portion thereof, does not block any part of one or more radiation transmission section portions 1301-B of the grid 1301, and the entire area(s) of one or more radiation transmission section portions 1301-B of the grid 1301 may be available for passage of radiation. The blocking of radiation by the shielding device 1302 or a portion thereof may be achieved by reflection or absorption.

The working conditions of the shielding device 1302 may include the position relative to the detector cell or the grid 1301, the angle relative to the detector cell or the grid 1301, the motion speed of the shielding device 1302 or a portion thereof, the motion direction of the shielding device 1302 or a portion thereof, or the like, or any combination thereof. In some embodiments, the movement of the shielding device 1302 may include a motion along a certain direction, e.g., the X-direction, the Y-direction, or the Z-direction. In some embodiments, the shielding device 1302 may tilt with respect to a certain axis or with respect to the grid 1301. When the whole or part of the shielding device 1302 is above the radiation transmitting portion 1301-B of the grid 1301, the shielding device or a portion thereof is in its extended position or partially extended position, and the radiation blocked or absorbed by the shielding device 1302 may cause a change of the respective active area of the detector cell.

The control module 220 in the system may control the working condition or position of the shielding device 1302, or a portion thereof (for example, one or more plates of the shielding device 1302 as illustrated in FIG. 13-A and FIG. 13-B), to adjust the active area of a detector cell, or the part of the radiation transmission portion 1301-B of the grid 1301 that may be available for passage of radiation. The control may be achieved by controlling a voltage, a current, an electric field, a magnetic field, or the like, or any combination thereof, that may be used to adjust the working condition or position of the shielding device 1302, or a portion thereof.

It should be noted that the above description about the shielding device is merely an example, and not intended to limit the scope of the present disclosure. For persons having ordinary skills in the art, various variations and modifications may be conducted under the teaching of the present disclosure. However, those variations and modifications may not depart from the protecting of the present disclosure. Exemplary variations may include that each grid may be equipped with one or more shielding devices, that multiple shield devices of a grid may be the same or different shielding devices, and that the dimensions of the shielding device of one grid may be the same as or different from that of another grid. The change of the working condition of the shielding device of one grid by way of the motion of the shielding devices or a portion thereof may be synchronized with or different from that of the second grid. The synchronization of the motion of two shielding devices or a portion thereof may include one or more characteristics including, for example, uniform rate or speed of the motion, uniform direction of the motion, uniform timing of the motion, or the like, or a combination thereof. For another example, the dimensions of the part of the shielding device in each transmitting portion of one grid may be the same or different. The change of the state of the shielding device in each transmitting portion of one grid may be the same or different. For instance, the shielding device relating to one grid may tilt with respect to an axis by a first angle, and the shielding device relating to another grid may tilt with respect to another axis by a second angle. As used herein, the first angle may be the same as or different from the second angle.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirits and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

I claim:

1. A system comprising:
  a radiation source comprising a plurality of focal spots located at different positions;
  a detector comprising a plurality of detector cells;
  a first grid located between the radiation source and the detector cells, the first grid comprising a plurality of radiation transmitting sections and a plurality of radiation absorbing sections; and
  a shielding device configured for adjustably blocking the radiation source, the shielding device being movably attached to a side of at least one of the plurality of radiation absorbing sections at a connecting point and being swinging around the connecting point by an angle;
  wherein
    at least one of the plurality of detector cells comprises an active area receiving radiation from the radiation source that passes through at least one of the plurality of radiation transmitting sections of the first grid,
    the radiation source, the first grid, the shielding device, and the detector cells are operatively coupled for detecting an object, and
    the active area is adjustable by adjusting at least one of the first grid, the shielding device, or a position of at least one of the plurality of focal spots of the radiation source.

2. The system according to claim 1, wherein the active area is adjustable by adjusting the position of the first grid or tilting the first grid by an angle.

3. The system according to claim 1, further comprising a second grid, the second grid being located between the first grid and the detector.

4. The system according to claim 3, the second grid comprising a plurality of radiation transmitting portions, and at least one of the plurality of radiation transmitting portions being coupled with the active area.

5. The system according to claim 4, the first grid and the second grid being moveable relative to each other.

6. The system according to claim 4, the active area being at least partially determined by the at least one of the plurality of radiation transmitting sections of the first grid and at least one of the plurality of radiation transmitting portions of the second grid.

7. The system according to claim 3, at least one of the plurality of radiation transmitting sections extending in a first direction.

8. The system according to claim 7, the first grid being moveable in a second direction perpendicular to the first direction.

9. The system according to claim 7, the second grid being moveable in the first direction.

10. The system according to claim 1, the detecting the object comprising scanning the object with radiation from at least two different focal spots of the radiation source.

11. The system according to claim 1, wherein the shielding device comprises one or more plates.

12. A method comprising:
  locating a first grid and a shielding device between a radiation source and a detector, the radiation source comprising a plurality of focal spots located at different positions, the detector comprising a plurality of detector cells, the first grid comprising a plurality of radiation transmitting sections and a plurality of radiation absorbing sections, the shielding device being movably attached to a side of at least one of the plurality of radiation absorbing sections at a connecting point and being swinging around the connecting point by an angle;
  emitting radiation from the radiation source toward the first grid; and
  receiving, on an active area of at least one of the plurality of detector cells, the radiation that passes through at least one of the plurality of radiation transmitting sections of the first grid;

wherein
the active area is adjustable by adjusting at least one of the first grid, the shielding device, or a position of at least one of the plurality of focal spots of the radiation source, and the radiation source, the first grid, the shielding device, and the detector cells are operatively coupled for detecting an object.

13. The method according to claim 12, wherein the active area is adjustable by adjusting the position of the first grid or tilting the first grid by an angle.

14. The method according to claim 12, further comprising locating a second grid between the first grid and the detector.

15. The method according to claim 14, the second grid comprising a plurality of radiation transmitting portions, and at least one of the plurality of radiation transmitting portions being coupled with the active area, wherein the active area is at least partially determined by the at least one of the plurality of radiation transmitting sections of the first grid and the at least one of the plurality of radiation transmitting portions of the second grid.

16. The method according to claim 15, the first grid and the second grid being moveable relative to each other.

17. The method according to claim 12, the at least one of the plurality of radiation transmitting sections extending in a first direction.

18. The method according to claim 17, further comprising moving the first grid in a second direction perpendicular to the first direction.

19. The method according to claim 17, further comprising moving the second grid in the first direction.

20. The method according to claim 12, wherein the shielding device comprises one or more plates.

* * * * *